| United States Patent [19] | [11] Patent Number: 4,824,849 |
| Baldwin et al. | [45] Date of Patent: Apr. 25, 1989 |

[54] α₂-ADRENOCEPTOR ANTAGONISTIC ARYLQUINOLIZINES

[75] Inventors: John J. Baldwin, Gwynedd Valley; Joel R. Huff, Lederach; Joseph P. Vacca, Telford; Steven D. Young, Lansdale; Jane deSolms, Norristown; James P. Guare, Jr., Quakertown, all of Pa.

[73] Assignee: Merck & Co., Inc., Rahway, N.J.

[21] Appl. No.: 90,641

[22] Filed: Aug. 28, 1987

Related U.S. Application Data

[60] Division of Ser. No. 848,262, Apr. 4, 1986, Pat. No. 4,710,504, which is a continuation-in-part of Ser. No. 740,609, Jun. 3, 1985, abandoned.

[51] Int. Cl.⁴ ................ A61K 31/415; A61K 31/305; C07D 455/00; C07D 471/20
[52] U.S. Cl. .................................... 514/267; 514/210; 514/219; 514/248; 514/250; 514/257; 514/278; 514/228.8; 514/230.8; 540/203; 540/353; 540/492; 540/493; 544/71; 544/231; 546/18
[58] Field of Search ............... 540/203, 353, 492, 493; 544/71, 231; 546/18; 514/210, 219, 234, 248, 250, 257, 267, 278, 228.8, 230.8

[56] References Cited

U.S. PATENT DOCUMENTS 4,710,504 12/1987 Baldwin et al. .................... 514/267

FOREIGN PATENT DOCUMENTS 1435573 5/1974 United Kingdom ................. 546/18
2106909 9/1982 United Kingdom ................. 546/18
2136804 9/1984 United Kingdom ................. 546/18

Primary Examiner—Mary C. Lee
Assistant Examiner—Zinna Northington
Attorney, Agent, or Firm—William H. Nicholson; Michael C. Sudol, Jr.

[57] ABSTRACT

Substituted hexahydro arylquinolizines and pharmaceutically acceptable salts thereof are selective α₂-adrenergic receptor antagonists and thereby useful as antidepressants, antihypertensives, ocular antihypertensives, antidiabetics, platelet aggregation inhibitors, antiobesity agents, and modifiers of gastrointestinal motility.

6 Claims, No Drawings

α₂-ADRENOCEPTOR ANTAGONISTIC ARYLQUINOLIZINES

This is a division of application Ser. No. 848,262, filed Apr. 4, 1986, now U.S. Pat. No. 4,710,504 which is in turn a continuation-in-part of application Ser. No. 740,609, filed June 3, 1985, now abandoned.

BACKGROUND OF THE INVENTION

This invention is concerned with novel substituted hexahydro arylquinolizines or pharmaceutically acceptable salts thereof which are selective $\alpha_2$-adrenoceptor antagonists and are of value in conditions where selective antagonism of the $\alpha_2$-adrenoceptor is desirable for example as antidepressant, antihypertensive, ocular antihypertensive, antidiabetic, antiobesity agents, platelet aggregation inhibitors, and modifiers of gastrointestinal motility. It also relates to processes for preparing the novel compounds, pharmaceutical compositions comprising the novel compounds and to a method of antagonizing $\alpha_2$-adrenoceptors.

The concept that the complex clinical state of depression is linked to a functional deficiency of monoamines in the central nervous system is now widely accepted. Numerous biochemical and clinical observations support the proposal that many forms of depressive illness are associated with reductions in adrenergic activity at functionally important sites in the brain. Thus, classical antidepressive drugs, such as amitriptyline and imipramine, are believed to act by blocking the neuronal reuptake of norepinephrine and/or serotonin, thereby enhancing the availability of the monoamines as neurotransmitters.

In addition to $\alpha_1$-adrenergic receptors which mediate postsynaptic responses to the neurotransmitter, norepinephrine, other adrenergic receptors are present at or near sympathetic terminals. These latter receptors, $\alpha_2$-adrenergic receptors, form part of a negative feedback system which modulates noradrenergic neurotransmission by controlling the impulse-induced release of norepinephrine from presynaptic terminals. Activation of $\alpha_2$-adrenergic receptors results in a decrease in the amount of norepinephrine normally released from the nerve terminals by nerve impulses while antagonism of $\alpha_2$-adrenergic receptors increases norepinephrine release. Therefore, molecules that block $\alpha_2$-adrenergic receptors afford an alternate approach to enhancement of noradrenergic function and the treatment of depression associated with an absolute or relative deficiency of adrenergic function.

$\alpha_2$-Adrenergic receptor antagonism is also associated with antidiabetic, antihypertensive, ocular antihypertensive, antiobesity, platelet aggregation inhibition activity, and modification of gastrointestinal motility.

Compounds structurally related to the novel compounds of this invention are disclosed in British Pat. Nos. 1,435,573 and 2,106,909 of John Wyeth and Brother, Ltd.

DETAILED DESCRIPTION OF THE INVENTION

This invention is concerned with a compound of structural formula I:

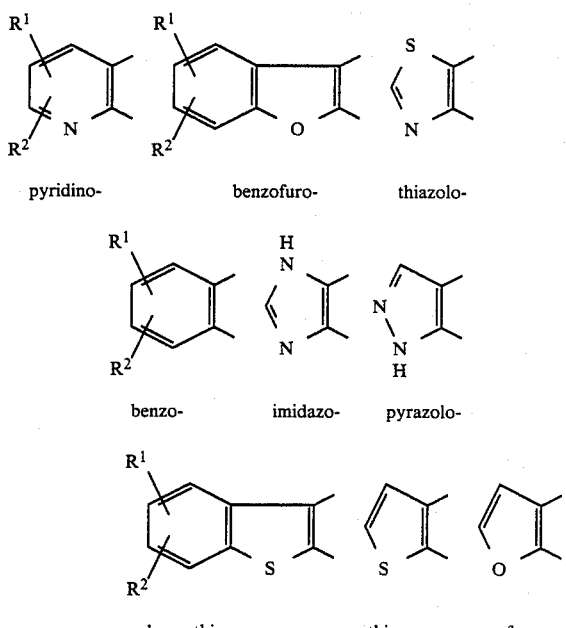

or a pharmaceutically acceptable salt thereof, wherein Ar represents an aromatic heterocycle such as:

pyridino-  benzofuro-  thiazolobenzo-  imidazo-  pyrazolobenzothieno-  thieno-  furo- $R^1$ and $R^2$ are independently,
(1) hydrogen,
(2) halo, such as chloro, bromo, or fluoro,
(3) hydroxy,
(4) $C_{1-3}$alkoxy, or
(5) $C_{1-6}$alkyl, either straight or branched chain;

B represents a spiroheterocycle of 4–7 members with up to 2 heteroatoms one of which is bonded to the spiro carbon and if Ar is benzo that heteroatom is nitrogen wherein the members are independently —CH₂—,

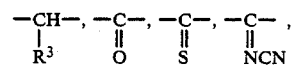

—O—, —NR3 or —SO₂— such as, (1)spiro-4-imidazolidin-2-one, (2)spiro-4-imidazolidin-2-thione, (3)spiro-3-(1,2,5-thiadiazolidin-1,1-dioxide), (4)spiro-5-pyrazolidin-3-one, (5)spiro-5-pyrrolidin-2-one, (6)spiro-5-tetrahydrofuran-2-one, (7)spiro-5-oxazolidin-2-one, (8)spiro-4-oxazolidin-2-one, (9)spiro-3-isoxazolidin-5-one, (10)spiro-4-imidazolidin-2,5-dione, (11)spiro-4-azetidin-2-one, (12)spiro-4-(5,6-dihydro-1H-pyrimidin-2(3H)-one), (13)spiro-4-(1,3-diazin-2,6-dione), (14)spiro-4-(3,4,5,6-tetrahydro-1,3-oxazin-2-one), (15)spiro-5-(2,4,5,6-tetrahydro-1,4-oxazin-3-one), (16)spiro-5-piperazin-2,3-dione, (17)spiro-5-piperazin-3-one, or (18)spiro-5-(1,4-diazepin-7-one).

$R^3$ is
(1) hydrogen,
(2)

wherein R is hydrogen or $C_{1-3}$ alkyl,
(3) $C_{1-6}$ alkyl, either unsubstituted or substituted with one or more of;
  (a) hydroxy,
  (b) carboxy,
  (c) $C_{1-3}$alkoxycarbonyl,
  (d) halo such as fluoro, chloro or bromo,
  (e) $C_{1-3}$alkoxy,
  (f) —$CONR^6R^7$ wherein $R^6$ and $R^7$ are the same or different and are hydrogen or $C_{1-5}$alkyl or joined together either directly to form a 5–7 membered ring such as pyrrolidino, or piperidino, or through a heteroatom selected from N, O, and S, form a 6-membered heterocycle with the nitrogen to which they are attached such as morpholino, piperazino, N—$C_{1-3}$ alkylpiperazino,
  (g) —$NR^6R^7$,
  (h)

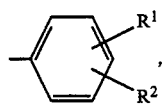

(i) —$SO_2NR^6R^7$; or (
  (j) —$SO_2(C_{1-3}alkyl)$;

$R^5$ is
(1) hydrogen,
(2) $C_{1-6}$ alkyl, either unsubstituted or substituted with one or more of
  (a) —$OR^8$, wherein $R^8$ is
    (i) H, or
    (ii) $C_{1-6}$alkyl,
  (b) $N(R^8)COR^8$, or
  (c) $CO_2R^8$,
(3) —$CO_2R^8$, or
(4) —$CONR^6R^7$.

The spiro-partial structures represented as B in Compound I, have the following structures:

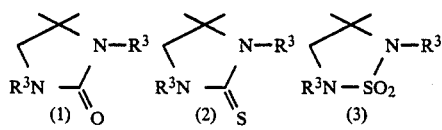

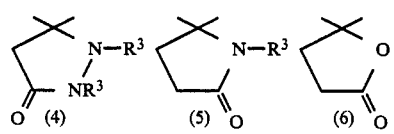

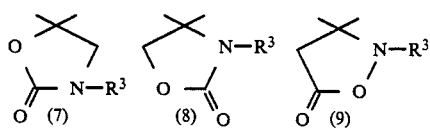

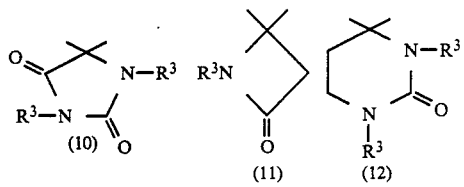

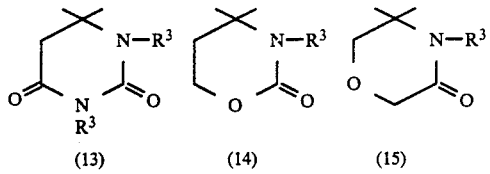

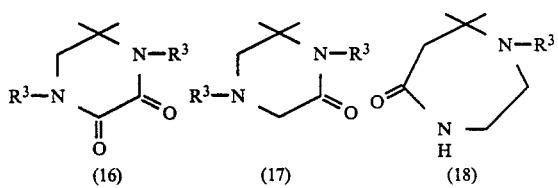

The pharmaceutically acceptable salts coming within the purview of this invention include the pharmaceutically acceptable acid addition salts. Acids useful for preparing these acid addition salts include, inter alia, inorganic acids, such as the hydrohalic acids (e.g., hydrochloric and hydrobromic acid), sulfuric acid, nitric acid, and phosphoric acid, and organic acids such as maleic, fumaric, tartaric, citric, acetic, benzoic, 2-acetoxybenzoic, salicylic, succinic, theophylline, 8-chlorotheophylline, p-aminobenzoic, p-acetamidobenzoic, methanesulfonic, or ethanedisulfonic acid.

In a preferred embodiment of this invention, Ar is $R^1,R^2$-benzo[b]furo-, $R^1,R^2$-benzo[b]thieno-, thieno-, furo- or benzo- and B is a spiro-4-imidazolidin-2-one or spiro-4-(5,6-dihydro-1H-pyrimidin-2(3H)-one). It is further preferred that $R^1$ and $R^2$ be hydrogen or halo and $R^3$ be $C_{1-6}$alkyl, especially methyl. It is also preferred that $R^5$ be hydrogen or $C_{1-6}$ alkyl.

It is most preferred that $R^1$ and $R^2$ be hydrogen, $R^3$ be methyl, and $R^5$ be hydrogen.

The novel compounds of this invention are described herein as having the configuration in which the heteroatom in ring B attached to carbon 2 and the hydrogen at 12b are trans-,

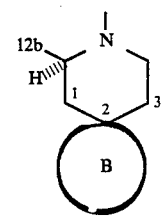

and it is the more preferred isomer for $\alpha_2$-adrenoceptor blockade activity. However, the isomers in which the heteroatom in ring B attached to carbon 2 and the hydrogen at 12b are cis are also active $\alpha_2$-adrenoceptor blockers and are considered to be within the scope of this invention. Each of these configurational isomers are racemates capable of being resolved into dextrorotatory and levorotatory enantiomers. This invention includes these pure enantiomers as well as all mixtures thereof, especially the racemates.

Another embodiment of this invention are the novel processes used to prepared the novel compounds.

For those compounds wherein the spiroheterocycle, B, includes a carbonyl or thiocarbonyl flanked on both sides by a heteroatom independently selected from oxygen and nitrogen, i.e. wherein B is an imidazolidin-2-one, or thione, oxazolidin-2-one or thione, or dihydropyrimidin-2-one or thione, or 2,6-dione a preferred process is to treat the 2,2-disubstituted quinolizine with carbonyldiimidazole or thiocarbonyldiimidazole as represented by the following:

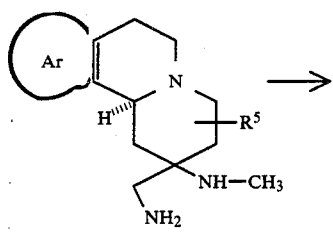

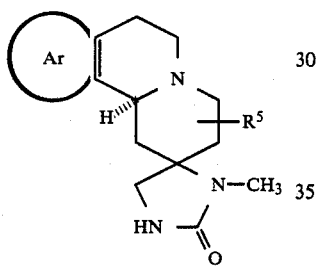

The reaction is conducted in an inert organic solvent such as benzene, toluene, chloroform, methylene dichloride, or the like or mixtures thereof at about 10° to 50° C. The temperature is not critical and the reaction is most readily conducted at room temperature. Reaction times of about 1 to about 10 hours are sufficient to complete the reaction, but longer times are not deleterious.

As an alternative to the carbonyl diimidazole and thiocarbonyldiimidazole there may be employed phosgene or thiophosgene respectively.

Similarly for those novel compounds wherein the spiroheterocycle includes a sulfonyl flanked on both sides by an oxygen or nitrogen such as a thiadiazolidin-1,1-dioxide, a 2,2-disubstituted quinolizine is treated with sulfuryl chloride as represented by the following:

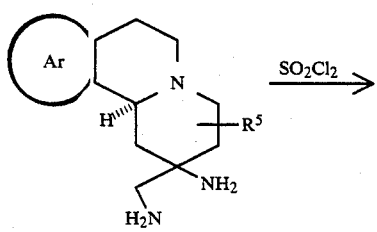

-continued

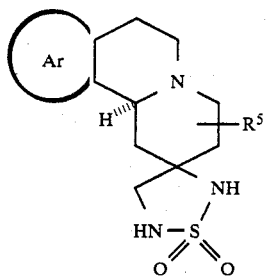

This reaction is best conducted in an inert atmosphere and solvent such as chloroform, methylene dichloride, benzene, toluene or the like at about $-10°$ to $+10°$ C., and preferably about 0° C. for about 1 to 8 hours followed by spontaneous warming to room temperature or about 20° C.

Another ring forming reaction useful for preparing the novel compounds of this invention comprises treating a quinolizin-2-one with a mixture of an organometallic such as n-butyl lithium and allyl-bis-(dimethylamino)phosphonate in an ethereal solvent such as THF, diethyl ether or 1,2-dimethoxyethane at about $-50°$ to $-20°$ C. followed by spontaneous warming to room temperature over about 2 to 5 hours. The reaction is depicted as follows:

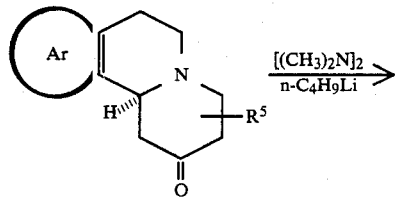

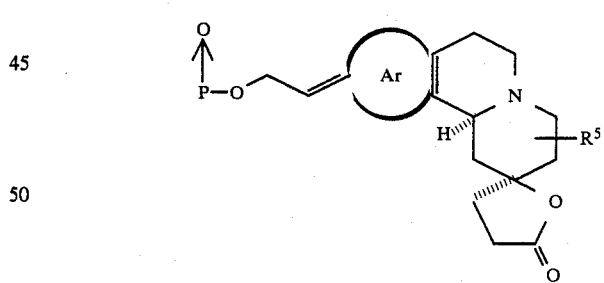

Spiro-imidazolidin-diones are prepared from 2-amino-2-alkoxycarbonylguinolizines by treatment with alkyl isocyanates depicted as follows:

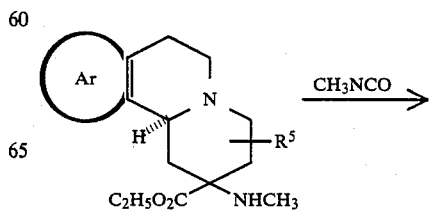

-continued

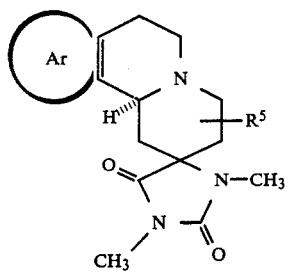

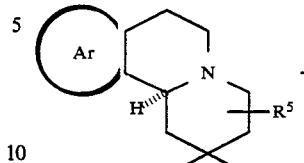

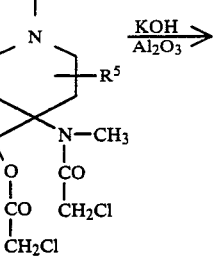

The reaction is conducted in an inert organic solvent such as acetonitrile, dioxane, chloroform, or the like preferably at about room temperature, although temperature is not critical, for about 12 to 24 hours.

Spiro-pyrazolidin-ones are prepared by treating a 2-alkoxycarbonylmethylenylquinolizine with hydrazine in an inert organic solvent such as benzene, toluene or the like at about 65°–100° C. for about 0.5 to 3 hours. The reaction is shown below:

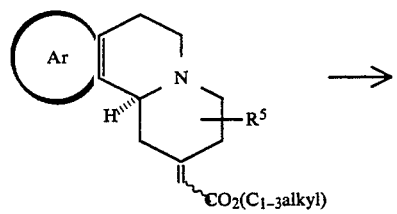

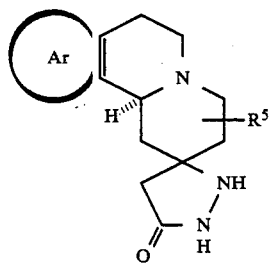

Similarly, using methylhydrazine in refluxing THF for about 18 to 48 hours there is produced the corresponding 2-methylpyrazolidin-3-one.

The same ester starting material with ethylenediamine in a lower alkanol such as methanol at about room temperature for about 20–60 hours provides a spiro-5-(1,4-diazepin-7-one).

The same ester starting material is useful in the synthesis of spiro-isoxazolidin-5-ones by treatment with N-alkyl hydroxylamine and an alkali metal carbonate such as potassium or sodium carbonate in an inert organic solvent such as THF, diethyl ether, or the like at about reflux temperature (30°–50° C.) for about 12 to 48 hours.

Treatment of a 2-amino-2-aminomethylquinolizine with diethyloxalate results in the formation of a spiro-piperazine-2,3-dione. The reaction is conducted in the same manner as that described for synthesis of the imidazolidinones.

Treatment of a 2-chloroacetoxymethyl-2-chloroacetylamino quinolizine with a mixture of finely divided potassium hydroxide and neutral alumina suspended in an inert organic solvent such as benzene or toluene at about ambient temperatures for about 1 to 4 hours provides a spiro-1,4-oxazin-3-one, as shown below:

In a similar reaction a 2-trifluoroacetylaminomethyl-2-chloroacetylaminoquinolizine is treated with potassium hydroxide pellets in a lower alkanol such as methanol or ethanol at ambient temperature for about 1 to 4 hours to yield a spiro-piperazin-3-one.

Another spirocycle of this invention is the 4-membered azetidinone and it is readily prepared by treating a spiro-isoxazolidin-5-one with hydrogen in the presence of a noble metal catalyst at a slightly elevated pressure of about 20 to 80 psig. at or near room temperature in a lower alkanol solvent for about 12 to 24 hours, or until the requisite amount of hydrogen is absorbed. The resulting amino acid is cyclized by treatment with dicyclohexylcarbodiimide (DCC). The ring size reduction is depicted as follows:

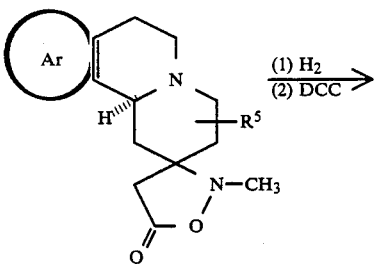

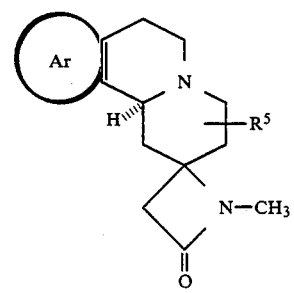

Any of the spiro-heterocycles with a secondary amino group as a member of the ring may be alkylated, or benzylated, or acylated by standard techniques well known to those skilled in the art.

In the novel method of this invention of selectively antagonizing $\alpha_2$-adrenergic receptors in a patient, a novel compound or pharmaceutically acceptable salt thereof, is administered in an amount ranging from about 0.01 to about 20 mg per kg of body weight per day, preferably from about 0.1 to about 10 mg per kg of body weight per day in a single dose or in 2 to 4 divided doses.

The novel compounds of this invention can be administered as the sole active ingredient or in combination with other antidepressants such as amitriptyline, imipramine or other norepinephrine or serotonin reuptake inhibitor or a monoamine oxidase inhibitor.

These doses are useful for treating depression, diabetes, hypertension, ocular hypertension, abnormal platelet aggregation, obesity and abnormal gastrointestinal motility.

The compounds, or pharmaceutically acceptable salts thereof, of the present invention, in the described dosages, are administered orally, intraperitoneally, subcutaneously, intramuscularly, transdermally or intravenously. They are preferably administered orally, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

EXAMPLE 1

(2RS,12bSR)-3'-methyl-spiro(1,3,4,6,7,12b-hexahydrobenzo[b]furo[2,3-a]quinolizine)-2,4'-imidazolidin-2'-one Step A: Preparation of 3-Cyanomethylbenzo[b]furan To a suspension of 2.64 gms (0.11 mole) of oil free sodium hydride in 200 ml of tetrahydrofuran (THF) was added dropwise a solution of 19.47 gms (0.11 mole) of diethylcyanomethylphosphonate in 75 mL of THF. After the $H_2$ evolution had ceased, a solution of 13.4 g (0.1 mole) of 3-(2H)-benzo[b]furanone in 100 mL of THF was added. The solution was heated at 70° C. for 1.5 hours, cooled, and poured into 500 mL of 5% HCl, and washed with ether. The ether phase was washed with brine, dried (MgSO$_4$), filtered and concentrated to give 15.4 g of a dark oil. The product was distilled at 96°-100° C./0.075 mm Hg to give 10.85 g of a yellow oil which crystallized upon standing.

Step B: Preparation of 2-(3-benzo[b]furanyl)ethylamine

A solution of 3.97 g (0.025 mole) of 3-cyanomethylbenzo[b]furan in 200 mL of diethyl ether was slowly added to a refluxing suspension of 3.84 g (0.1 mole) of lithium aluminum hydride in 400 mL of ether. The reaction was heated 3 hours., cooled and water was slowly added. The suspension was filtered through a pad of filter aid and the filtrate was evaporated to give 3.2 g of oily product. The hydrochloride salt has m.p. 183°-185° C.

Step C: Preparation of 3-(2-Formamidoethyl)benzo[b]furan

A solution of 2.35 g (0.015 mole) of 2-(3-benzo[b]furanyl)ethylamine and 5 mL of ethyl formate was heated at 60° C. for 3 hours, into 2N HCl and washed with methylene chloride which in turn was washed with 5% sodium hydroxide (w/v), dried (MgSO$_4$), filtered and concentrated to give 2.70 g of product.

Step D: Preparation of 3,4-dihydrobenzo[b]furo[2,3-c]pyridine 2.28 Grams (0.012 mole) of 3-(2-formamidoethyl)benzo[b]furan was added to 28 g of polyphosphoric acid which was preheated to 100° C. After 1-1.5 hours, the reaction mixture was poured onto ice and the residues were washed with water. The polyphosphoric acid was dissolved in water, filtered through a pad of celite and made basic with concentrated ammonia. A precipitate was collected and dried to give 1.45 g of product, m.p. 170°-171° C.

Step E: Preparation of (12b-SR)-1,3,4,6,7,12b-Hexahydrobenzo[b]furo[2,3-a]quinolizin-2-one To a solution of 12 g (0.070 mol) of 3,4-dihydrobenzo[b]furo[2,3-c]pyridine dissolved in 500 mL of acetonitrile at 60° C. was added 20 g (0.140 mol) of 2-trimethylsiloxy-1,3-butadiene followed by 13.6 g (0.10 mol) of anhydrous zinc chloride. The mixture was heated at 60° C. for 1.5 hour, cooled to 25° C., and 30 mL of 5% HCl was added and stirred 10 minutes. 40% Sodium hydroxide was added until the reaction was basic; 200 mL of water was added; and the acetonitrile layer was separated. The aqueous layer was filtered through celite and washed with ether. The combined organic layers were dried (Na$_2$SO$_4$), filtered, and concentrated to a brown residue which was chromatographed (silica, ethyl acetate/hexane (1:1)) to give 8.2 g of product, m.p. 108°-9° C.

Resolution of (12bSR)-1,3,4,6,7,12b-hexahydrobenzo[b]furo[2,3-a]quinolizin-2-one A solution of (−)-di-p-toluoyl-L-tartaric acid monohydrate (25.9 g) in 100 ml of ethyl acetate was mixed with a solution of (12bSR)-1,3,4,6,7,12b-hexahydrobenzo[b]furo[2,3-a]quinolizin-2-one (15.5 g) in 700 ml of ethyl acetate and allowed to stand 12–78 hours. The mixture was filtered to yield 21 g of the di-p-toluoyl-L-tartrate salt of the amine. The free base was liberated by partitioning between aqueous Na$_2$CO$_3$ and ethyl acetate ($[\alpha]_D$=ca. −79°; C=1; CHCl$_3$). The diasteriomeric salt of this material was again prepared following the above procedure. The collected di-p-toluoyl-L-tartrate salt was partitioned between ethyl acetate and aqueous Na$_2$CO$_3$, dried (Na$_2$SO$_4$), filtered, treated with charcoal, filtered and evaporated to yield 5.4 g (35%) of (12bS)-1,3,4,6,7,12b-hexahydrobenzo[b]furo[2,3-a]quinolizin-2-one; $[\alpha]_D$=−84°; (C=1, CHCl$_3$).

The (12bR)-1,3,4,6,7,12b-hexahydrobenzo[b]furo[2,3-a]quinolizin-2-one was obtained by substituting (+)-di-p-toluoyl-D-tartaric acid monohydrate for (−)-di-p-toluoyl-L-tartaric acid in the above procedure to provide product with $[\alpha]_D$=+84° (C=1, CHCl$_3$).

Employing the procedures substantially as described in Example 1, Steps A through E/F, or in some cases, Steps C through E/F but substituting for the 3-benzofuranone used in Step A thereof the ketones described in Table I, or for the ethylamines used in Step C thereof, the corresponding ethylamines described in Table I, or for the butadienes used in Step E thereof, the corresponding substituted butadienes described in Table I, there are prepared the Ar[2,3-a]quinolizin-2-ones, also described in Table I by the following reactions:

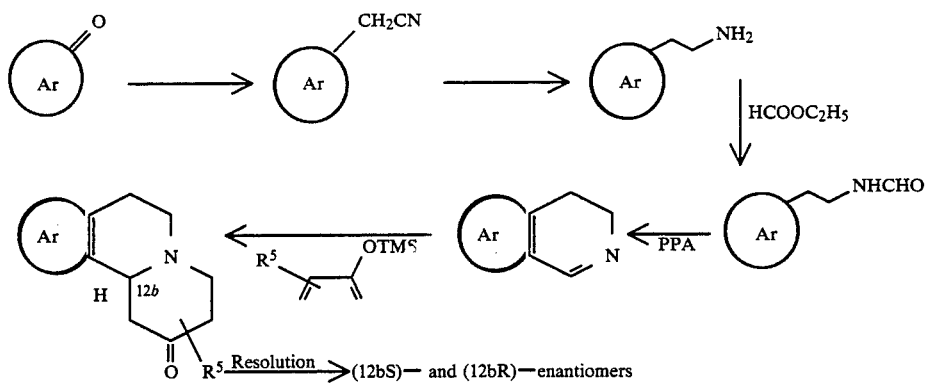

TABLE I

| Ar | R⁵ | Ar | R⁵ |
|---|---|---|---|
| 10-chlorobenzo-[b]furo- | H | benzo[b]thieno- | 1-CH₃ |
| thieno- | H | 10-methylbenzo-[b]thieno- | 4-COOCH₃ |
| furo- | 3-CH₃ | 9-methoxybenzo-[b]thieno- | H |
| 11-hydroxy-benzo[b]furo | H | 11-fluorobenzo-[b]furo- | H |
| 10,11-dimethyl-benzo[b]furo- | H | 9-bromobenzo-[b]furo- | 1-CON(CH₃)₂ |
|  |  | 11-methoxybenzo-[b]furo- | H |
| pyridino- | H | thiazolo- | H |
| imidazo | H | pyrazolo- | H |

Step F: Preparation of (2RS,12bSR)-2-aminomethyl-2-methylamino-1,3,4,6,7,12b-hexahydrobenzo[b]furo[2,3-a]quinolizine Into a 1000 ml flask was placed 7 g (29 mmol) of 1,3,4,6,7,12b-hexahydrobenzo[b]furo[2,3-a]quinolizin-2-one in 500 ml dry THF which had previously been saturated with dry methylamine at 0° C. To this mixture was added 10.44 g (64 mmol) of diethyl cyanophosphonate. After stirring for 18 hours, the solvent was removed and the resultant crude amononitrile was dissolved in 300 ml dry THF and treated with 145 ml 1M borane in THF. This mixture was refluxed for 18 hours, cooled and quenched by the slow addition of methanol until ebulition ceased, after which 400 ml 6N HCl was added and the reaction mixture was refluxed for an additional 2 hours. After cooling, the solvent was removed and the residue was basified by the addition of 400 ml saturated Na₂CO₃ solution. This was extracted with 5 × 100 ml CHCl₃. The combined organic extracts were dried (Na₂SO₄) and the solvent was evaporated. Medium pressure column chromatography (chloroform saturated with ammonia) yielded 0.552 g. (7%) (2SR,12bSR)-2-aminomethyl-2-methylamino-1,3,4,6,7,12b-hexahydrobenzo[b]furo[2,3-a]quinolizine as a yellow oil, followed by 4.9 g of the desired product (62%) (2RS,12bSR)-2-aminomethyl-2-methylamino-1,3,4,6,7,12b-hexahydrobenzo[b]furo[2,3-a]quinolizine, also as a yellow oil.

Similarly prepared are the (2R,12bs)- and (2S,12bR) enantiomers by starting with the enantiomeric quinolizin-2-ones described in Step E.

Step G: Preparation of (2RS,12bSR)-3'-methyl-spiro(1,3,4,6,7,12b-hexahydrobenzo[b]furo-[2,3-a]quinolizin)-2,4'-imidazolidin-2'-one Into a 400 ml flask was placed 4.4 g (15.8 mmol) of (2RS,12bSR)-2-aminomethyl-2-methylamino-1,3,4,6,7,12b-hexahydrobenzo[b]furo[2,3-a]-quinolizine from Step F in 200 ml toluene. To this was added 5 g (32 mmol) of 1,1'-carbonyldiimidazole and the reaction was stirred for 5 hours, after which the toluene was washed with 3 × 50 ml H₂O, 50 ml brine, dried (Na₂SO₄) and the solvent evaporated to obtain a yellow solid. This material was dissolved in hot ethyl acetate, decolorized, filtered and treated with ethanolic HCl to give 3.53 g (72%) of (2RS,12bSR)-3'-methyl-spiro(1,3,4,6,7,12b-hexahydrobenzo[b]furo[2,3-a]quinolizin)-2,4'-imidazolidin-2'-one as a white crystalline hydrochloride salt which was recrystallized from methanol/ethyl acetate: m.p. 220° C. (dec).

Similarly prepared are the (2R,12bs)- and (2S,12bR)-enantiomers of the 3'-methylimidazolidin-2'-one by starting with the enantiomeric diamines described in Step F hereof.

Employing the procedure substantially as described in Example 1, Steps F and G but substituting for the 2-aminomethyl-2-methylamino-1,3,4,6,7,12b-hexahydrobenzo[b]furo[2,3-a]quinolizine and methylamine used in Step F thereof an equimolar amount of the quinolizin-2-ones described in Table I and R³NH₂, there are prepared the spiro-imidazolidin-2-ones described in Table II in accordance with the following reaction scheme:

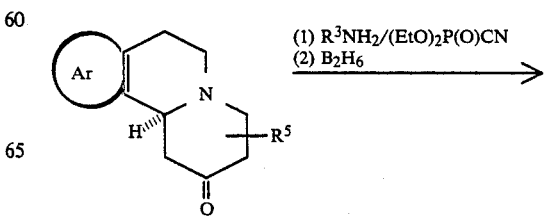

-continued

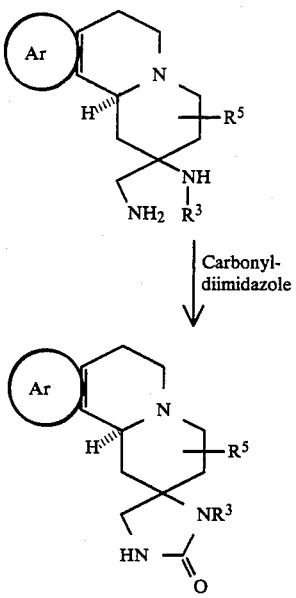

TABLE II

| Ar | R⁵ | R³ | Ar | R⁵ | R³ |
|---|---|---|---|---|---|
| 10-chlorobenzo-[b]furo- | H | —CH₃ | benzo[b]thieno- | 1-CH₃ | —CH₃ |
| thieno | H | H | 10-methylbenzo-[b]thieno- | 4-COOCH₃ | —CH₃ |
| furo | 3-CH₃ | —C₂H₅ | 9-methoxybenzo-[b]thieno- | H | H |
| 11-hydroxy-benzo[b]furo | H | —C₃H₇ | 11-fluorobenzo-[b]furo- | H | H |
| 10,11-dimethyl-benzo[b]furo- | H | —CH₃ | 9-bromobenzo-[b]furo- | 1-CON(CH₃)₂ | PhCH₂— |
|  |  |  | 11-methoxybenzo-[b]furo- | H | H |
| pyridino- | H | —CH₃ | thiazolo- | H | CH₃ |
| imidazo | H | —CH₃ | pyrazolo- | H | CH₃ |

EXAMPLE 2

(2RS,12bSR)-spiro(1,3,4,6,7,12b-hexahydrobenzo[b-]furo[2,3-a]quinolizin)-2,4'-imidazolidin-2'-one Step A: Preparation of (2RS,12bSR)-2-aminomethyl-2-amino-1,3,4,6,7,12b-hexahydrobenzo[b]furo[2,3-a]quinolizine Employing the procedure substantially as described in Example 1, Step F, but substituting for the methylamine used therein, an equimolecular amount of ammonia, there was produced the title compound in comparable yield which was used directly in the next step without characterization.

Step B: Preparation of (2RS,12bSR)-spiro(1,3,4,6,7,12b-hexahydro[b]furo[2,3-a]quinolizin)-2,4'-imidazolidin-2'-one The mixture of 540 mg of the diamine from Step A and 648 mg of 1,1'-carbonyldiimidazole in 200 ml of toluene was stirred overnight under N₂. To this reaction mixture, 10 ml of H₂O was added and stirred for 10 minutes. A precipitated solid was collected by filtration and transformed into HCl salt. The salt was recrystallized from MeOH-CHCl₃, yield 80 mg, m.p. 270° C.

Employing the procedure substantially as described in Example 1, but substituting for the methylamine used therein an equimolecular amount of n-propylamine, there are produced in sequence:
(2RS,12bSR)-2-aminomethyl-2-n-propylamino-1,3,4,6,7,12b-hexahydrobenzo[b]furo[2,3-a]quinolizine, and
(2RS,12bSR)-3'-n-propyl-spiro(1,3,4,6,7,12b-hexahydrobenzo[b]furo[2,3-a]quinolizin)-2,4'-imidazolidin-2'-one.

EXAMPLE 3

(2RS,12bSR)-1',3'-dimethyl-spiro(1,3,4,6,7,12b-hexahydrobenzo[b]furo[2,3-a]quinolizin)-2,4'-imidazolidin-2'-one Into a 125 ml Erlenmeyer flask was placed 0.225 g (0.72 mmol) (2SR,12bRS)-3'-methyl-spiro(1,3,4,6,7,12b-hexahydrobenzo[b]furo-[2,3-a]quinolizin)-2,4'-imidazolidin-2'-one (Example 1) in 50 ml toluene followed by 50 ml 40% NaOH, 0.366 g (1.08 mmol) tetrabutylammonium hydrogen sulfate end, with vigorous stirring, 0.067 ml (1.08 mmol) methyl iodide. Stirring was continued for 2 hours, after which the toluene layer was separated and washed with 3×50 ml H₂O, 50 ml brine, dried (Na₂SO₄) and the solvent was removed to obtain 0.2 g (85%) pure (2RS,12bSR)-1',3'-dimethyl-spiro(1,3,4,6,7,12b-hexahydrobenzo[b]furo[2,3-a]quinolizin)-2,4'-imidazolin-2'-one. This was dissolved in 50 ml ethyl acetate and ethanolic HCl was added to give a white crystalline hydrochloride salt: m.p. 260° C. (dec.).

Employing the above procedure but starting with the enantiomers of the 3'-methylimidazolidin-2'-one described in Example 1, Step G, there were produced the (2R,12bS)- and (2S,12bR)-enantiomers of the title compound with [α]$_D$ +1° (C=1.0 CH₃OH), and [α]$_D$ −1° (C=1.0 CH₃OH) respectively.

EXAMPLE 4

(2RS,12bSR)-1'-ethyl-3'-methyl-spiro[1,3,4,6,7,12b-hexahydrobenzo[b]furo[2,3-a]quinolizin]-2,4'-imidazolidin-2'-one·HCl 0.25H₂O To a solution of the 3'-methylimidazoline compound from Example 1 (0.1 g, 0.32 mmol) in 20 ml of toluene was added tetrabutylammonium hydrogen sulfate (0.163 g, 0.48 mmol), 20 mls of 40% sodium hydroxide solution, and, with vigorous stirring, ethyl iodide (0.075 g, 0.48 mmol). This was stirred for 18 hours and then the toluene layer was separated and washed with 3×30 ml of water, 30 ml of brine, dried (Na$_2$SO$_4$) filtered and concentrated to give an oil which was chromatographed (silica, ethyl acetate) to give the product as the HCl 0.25H$_2$O, m.p. 235°–239° C.

EXAMPLE 5

(2RS,12bSR)-3'-methyl-1'-propyl-spiro[2,3,4,6,7,12b-hexahydrobenzo[b]furo[2,3-a]quinolizin]-2,4'-imidazolidin-2'-one HCl To a solution of the 3'-methylimidazoline compound from Example 1 (0.1 g, 0.32 mmol) in 20 ml of toluene was added tetrabutylammonium hydrogen sulfate (0.163 g, 0.48 mmol), 20 mls of 40% sodium hydroxide solution, and, with vigorous stirring, N-propyl iodide (0.110 g, 0.64 mm). This was stirred for 5 hours and then the toluene layer was separated and washed with 3×30 ml of water, 30 ml of brine, dried (Na$_2$SO$_4$), filtered and concentrated to give an oil which was chromatographed (silica, ethyl acetate) to give the product as the HCl; m.p. 240°–242° C.

EXAMPLE 6

(2RS,12bSR)-1'-hydroxyethyl-3'-methyl-spiro[1,3,4,6,7,12-b-hexahydrobenzo[b]furo[2,3-a]quinolizin]-2,4'-imidazolidin-2'-one HCl, 0.25H$_2$O Step A: Preparation of 2-methoxy-2-(2-iodoethoxy)propane To 6 mls of cold (0° C.) methoxypropene was added 3 mls of 2-iodoethanol and 1 drop of phosphorous oxychloride (POCl$_3$). The reaction was stirred for 1 hour and then solid potassium carbonate was added. After 10 minutes the liquid was decanted and concentrated to give the product as an oil.

Step B: (2RS,12bSR)-1'-hydroxyethyl-3'-methyl-spiro[1,3,4,6,7,12b-hexahydrobenzo[b]furo[2,3-a]quinolizin]-2,4'-imidazolidin-2'-one HCl, 0.25H$_2$O To a solution of the 3'-methylimidazolidine from Example 1 (0.04 g, 0.16 mmol) in 20 ml of toluene was added tetrabutylammonium hydrogen sulfate (0.082 g, 0.24 mmol), 20 mls of 40% sodium hydroxide solution, and, with vigorous stirring, 2-methoxy-2-(2-iodoethoxy)propane (0.053 g, 0.209 mmol). This was stirred for 45 hours and then the toluene layer was poured into 20 mls of 5% HCl solution, stirred for 15 minutes and then made basic. The toluene layer was separated and washed with 3×30 ml of water, 30 ml of brine, dried (Na$_2$SO$_4$) filtered and concentrated to give an oil which was chromatographed (silica, NH$_3$/saturated CHCl$_3$) to give the product as the HCl, (0.25H$_2$O; m.p. 172°–176° C.

EXAMPLE 7

(2RS,12bSR)-1'-Benzyl-3'-methyl-spiro[1,3,4,6,,7,12b-hexahydrobenzo[b]furo[2,3-a]quinolizin]-2,4'-imidazolidin-2'-one HCl, 0.25H$_2$O To a solution of the 3'-methylimidazolidine compound from Example 1, (0.1 g, 0.32 mmol) in 20 ml of toluene was added tetrabutylammonium hydrogen sulfate (0.163 g, 0.48 mmol), 20 mls of 40% sodium hydroxide solution, and, with vigorous stirring, benzyl bromide (0.123 g, 0.720 mmol). This was stirred for 5 hours and then the toluene layer was separated and washed with 3×30 ml of water, 30 ml of brine, dried (Na$_2$SO$_4$) filtered and concentrated to give an oil which was chromatographed (silica, ethyl acetate) to give the product as the HCl, 0.25H$_2$O; m.p. 245°–248° C.

EXAMPLE 8

(2RS,12bSR)-1'-acetyl-3'-methyl-spiro[1,3,4,6,7,12b-hexahydrobenzo[b]furo[2,3-a]quinolizin]-2,4'-imidazolidin-2'-one HCl, 0.25H$_2$O To a solution of the 3'-methylimidazolidine from Example 1 (0.255 g, 0.5 mmol) in 15 ml of THF (0° C.) was added 0.345 mls of a 1.6M n-butyl lithium solution (0.55 mmol). After 15 minutes the reaction was cooled to −78° C. and acetyl chloride (0.050 g, 0.64 mmol) was rapidly added. Stirring was continued at −78° C. for 30 minutes and the temperature was then raised to 25° C. over 2 hours. The reaction mixture was then poured into 30 ml of water, extracted with 2×20 ml of ethyl acetate, dried (Na$_2$SO$_4$), filtered and concentrated to an oil which was chromatographed (silica, ethyl acetate) to give the product as the HCl, 0.25H$_2$O; 251°–255° C.

EXAMPLE 9

(2RS,12bSR)-1'-acetyl-3'-propyl-spiro(1,3,4,6,7,12b-hexahydrobenzo[b]furo[2,3-a]quinolizin)-2,4'-imidazolidin-2'-one Employing the procedure substantially as described in Example 8, but substituting for the 3'-methylimidazoline compound used in Example 8, an equimolecular amount of the corresponding 3'-propylimidazolidine compound, there is obtained, the title compound in comparable yield.

EXAMPLE 10

(2RS,12bSR)-1'-methyl-3'-propyl-spiro(1,3,4,6,7,12b-hexahydrobenzo[b]furo[2,3-a]quinolizin)-2,4'-imidazolidin-2'-one Employing the procedure substantially as described in Example 3, but substituting for the 3'-methylimidzolidine compound used in Example 3, an equimolecular amount of the corresponding 3'-propylimidazoline compound, there is obtained, the title compound in comparable yield; m.p. 220°–225° C.

EXAMPLE 11

(2RS,12bSR)-3'-methyl-spiro(1,3,4,6,7,12b-hexahydrobenzo[b]furo[2,3-a]quinolizin)-2,4'-imidazolidin-2'-thione (2RS,12bSR)-2-Aminomethyl-2-methylamino-1,3,4,6,7,12b-hexahydrobenzo[b]furo[2,3-a]quinolizine (285 mg, 1 mmole) and 1,1'-thiocarbonyldiimidazole (356 mg, 2 mmole) were stirred in toluene (20 ml) at ambient temperature for 2 hours then at 80° C. for 2 hours. The reaction mixture was concentrated to dryness, dissolved in CH$_2$Cl$_2$, washed with H$_2$O, saturated NaCl solution, and dried (Na$_2$SO$_4$). Filtration and concentration to dryness provided 88 mg (27%) of the subject compound after chromatography. Treatment with ethanolic HCl provided the hydrochloride salt; m.p. 280° C.

Anal. for C$_{18}$H$_{21}$N$_3$OS.HCl.½H$_2$O: calc'd.: C, 57.98; H, 6.22; N, 11.27. Found: C, 58.15; H, 6.23; N, 11.10.

EXAMPLE 12

(2RS,12bSR)-2'-methyl-spiro(1,3,4,6,7,12b-hexahydrobenzo[b]furo-[2,3-a]quinolizin)-2,3'-(1,2,5-thiadiazolidin-1',1'-dioxide), HCl A mixture of 570 mg of the diamine from Example 1, Step F, and 1 ml of triethylamine in 20 ml of CHCl₃ was stirred at −78° C. under N₂. Sulfuryl chloride (323 mg) in 10 ml of CHCl₃ was added dropwise. The mixture was stirred at −78° C. for 1 hour and at room temperature. Evaporation gave an oily residue which was redissolved in CHCl₃, washed with H₂O, dried over K₂CO₃, and evaporated to dryness. The product was purified by spinning disk chromatography and transformed into the HCl salt with ethanolic hydrogen chloride. Recrystallization from ethanol-ether gave 15 mg of product; m.p. 250° C.

EXAMPLE 13

(2RS,12bSR)-3'-Methyl-spiro(1,3,4,6,7,12b-hexahydrobenzo[b]thieno[2,3-a]quinolizin)-2,4'-imidazolidin-2'-one To a three necked, oven dried round bottomed flask with stirring bar was added 100 ml of dry THF. The flask and its contents were cooled in an ice bath to 0° C. and the THF was saturated with methylamine gas. To this solution was added 590 mg of 1,3,4,6,7,12b-hexahydrobenzo[b]thieno[2,3-a]quinolizin-2-one and 816 mg of diethylcyanophosphate under the protection of a calcium sulfate drying tube. The ice bath was allowed to expire and the mixture was stirred overnight at room temperature. The reaction mixture was concentrated in vacuo, and redissolved in 50 ml of dry THF to which was added 25 ml of 1.0M borane-THF complex, under argon. This mixture was heated at reflux overnight. The cooled reaction mixture was quenched with 3 ml of methanol, then 20 ml of 2N HCl were added and the THF was removed in vacuo. The aqueous residue was made basic with concentrated ammonium hydroxide and extracted with chloroform (2×25 ml). The combined chloroform extracts were dried over anhydrous potassium carbonate, filtered and concentrated in vacuo. Chromatography of the crude product on 20 g of silica gel with 2.5% methanol in ammonia saturated chloroform as eluant provided 170 mg of intermediate diamine.

To a 100 ml round bottomed flask containing 170 mg of the aforementioned diamine was added 3 ml of chloroform and 15 ml of toluene. To this solution was added 406 mg of carbonyldiimidazole and the mixture was stirred overnight at room temperature. The reaction mixture was diluted with 100 ml of ethyl acetate and was washed with water and brine. Drying (potassium carbonate), filtration and removal of the solvent in vacuo left an off-white solid. Chromatography of this material on 20 g of silica gel with ammonia saturated chloroform provided 83 mg of the title compound as a crystalline solid. An analytical sample was prepared by recrystallization from ethanol-ethyl acetate; m.p. 290° C. (dec.).

EXAMPLE 14

(2RS,12bSR)-1',3'-Dimethyl-spiro(1,3,4,6,7,12b-hexahydrobenzo[b]thieno[2,3-a]quinolizine)-2,4'-imidazolidin-2'-one To a 50 ml round bottomed flask was added (2RS,12bSR)-3'-methyl-spiro(1,3,4,6,7,12b-hexahydrobenzo[b]thieno[2,3-a]quinolizine)-2,4'-imidazolidin-2'-one and 10 ml of toluene. When the material had dissolved, 10 ml of 10N sodium hydroxide and 44 mg of tetrabutylammonium sulfate were added. While stirring vigorously, 8.1 microliters of methyl iodide was added.

The mixture was stirred for 30 minutes at room temperature. The layers were separated and the toluene layer was washed with water and brine. Drying (potassium carbonate), filtration and removal of the solvent in vacuo left 29 mg of crude product. This material was chromatography on 3 g of silica gel with 3% (V/V) methanol in chloroform. The oil thus obtained was triturated with ethyl acetate and the crystals that precipitated were collected on a frit and dried overnight at 70° C./0.05 torr giving 25 mg of the title compound; m.p. 204°–206° C.

EXAMPLE 15

(2RS,12bSR)-3'-Methyl-spiro(10-methyl-1,3,7,12b-hexahydrobenzo[b]thieno[2,3-a]quinolizine)-2,4'-imidazolidin-2'-one To an oven dried 100 ml round bottomed flask with stirring bar, argon inlet and a gas dispersion tube was added 75 ml of dry THF. The contents of the flask were cooled to 0° C. and saturated with methylamine gas. To this solution was added 400 mg of 10-methyl-1,3,4,6,7,12b-hexahydrobenzo[b]thieno [2,3-a]quinolizin-2-one and 0.491 ml of diethylcyanophosphonate. The ice bath was allowed to expire and the mixture was stirred at room temperature overnight. The entire mixture was concentrated in vacuo and redissolved in THF. To this solution was added 10.2 ml of a 0.98M solution of borane-THF complex with a syringe. This mixture was heated at reflux over night. The cooled reaction mixture was quenched with methanol and concentrated to a colorless syrup in vacuo. This material was stirred with 100 ml of 2N HCl over night. The HCl solution was washed with ether, made basic with 20% NaOH, and extracted with chloroform (2×75 ml). The combined chloroform extracts were washed with brine and dried over anhydrous potassium carbonate. Filtration and removal of the solvent left 231 mg of a colorless oil. This material was chromatographed on 30 g of silica gel with 5% methanol in ammonia saturated chloroform as eluant. This chromatography provided 51 mg of the intermediate diamine.

To a 100 ml round bottomed flask containing the aforementioned diamine (51 mg) was added 1.0 ml of dry chloroform. When the material had dissolved, 5 ml of toluene was added followed by 81 mg of carbonyl diimidazole. This mixture was stirred overnight at room temperature under argon. The reaction mixture was diluted with 30 ml of ethyl acetate and washed with water (2×15 ml) and brine (25 ml). Drying over magnesium sulfate, filtration and removal of the solvent in vacuo left 60 mg of a solid which was chromatographed on 5 g of silica gel with ammonia saturated chloroform to give 28.6 mg of the title compound which crystallized on trituration with ethyl acetate; m.p. 225° C. (dec.)

EXAMPLE 16

(2RS,12bSR)-3'-Methyl-spiro(11-chloro-1,3,4,6,7,12b-hexahydrobenzo[b]thieno[2,3-a]quinolizine)-2,4'-imidazolidin-2'-one Step A: Preparation of (2RS,12bSR)-2-Aminomethyl-2-methylamino-11-chloro-1,3,4,5,7,12b-hexahydrobenzo[b]thieno[2,3-a]quinolizine 11-chloro-1,3,4,6,7,12b-hexahydrobenzo[b]thieno[2,3-a]quinolizin-2-one (500 mg, 1.71 mmole) was added to dry tetrahydrofuran (100 ml) saturated with methylamine with stirring at 0° C. Diethyl cyanophosphonate (0.7 ml, 4.6 mmole) was added; the solution was stoppered and left to stir at ambient temperature for 18 hours. The solvent was removed and the residue partitioned between ethyl acetate and H₂O. The organic layer was separated, washed with H₂O, saturated NaCl solution, and dried (Na₂SO₄). Filtration and concentration provided the aminonitrile which was immediately dissolved in fresh tetrahydrofuran (100 ml) and treated with borane in tetrahydrofuran (0.98M, 10.42 ml, 10.4 mmole). After stirring at ambient temperature for 15 minutes the reaction mixture was heated at reflux for 18 hours. After cooling, methanol was added slowly to destroy excess borane, 6N HCl (80 ml) was added and the mixture was heated at reflux for 2 hours. After cooling the reaction mixture was basified with solid NaOH, extracted with CH₂Cl₂, dried (Na₂SO₄), filtered and concentrated to give 310 mg (54%) of title compound after chromatography.

Step B: Preparation of (2RS,12bSR)-3'-Methyl-spiro(11-chloro-2,3,4,6,7,12b-hexahydro-2H-benzothieno[2,3-a]quinolizine)-2,4'-imidazolidin-2'-one (2RS, 12bSR)-2-Aminomethyl-2-methylamino-11-chloro-1,3,4,6,7,12b-hexahydrobenzo[b]thieno[2,3-a]quinolizine (270 mg, 0.8 mmole) and 1,1'-carbonyldiimidazole (254 mg, 1.6 mmole) were dissolved in toluene (100 ml) and stirred at ambient temperature under N₂ for 5 hours. Water was added; the organic layer was separated, washed with H₂O, saturated NaCl solution and dried (Na₂SO₄). Filtration and concentration followed by chromatography provided 140 mg (42%) of the subject compound. Treatment with ethanolic HCl gave the hydrochloride salt, m.p. 322°–325° C.

Anal. for $C_{17}H_{20}ClN_3OS \cdot HCl \cdot H_2O$: Calc'd: C, 51.92; H, 5.58; N, 10.09. Found: C, 51.94; H, 5.34; N, 9.80.

EXAMPLE 17

(2RS,12bSR)-spiro[1,3,4,6,7,12b-hexahydrobenzo[b]furo [2,3-a]quinolizin]2,5'-tetrahydrofuran-2'-one HCl, 0.25 H₂O To 2.85 ml of 2.6M n-butyllithium (4.0 mmol) at −40° C. was added a solution of allyl-bis-dimethylamino phosphonate in 0.5 ml of THF. The temperature was raised to −20° C. and stirring was continued for 2 hours, after which a solution of 1,3,4,6,7,12b-hexahydrobenzo[b]furo [2,3-a]quinolizin-2-one in 1 ml of THF was added. The reaction was allowed to come to room temperature, stirred for 2.5 hours and was poured into 50 mls of water which was extracted with 2×30 ml of ethyl acetate, dried (Na₂SO₄), filtered and concentrated to give a residue which was chromatographed (silica, ethyl acetate) to give the product. Treatment with ethanol-HCl gave the HCl 0.25 H₂O salt, m.p. 258°–262° C.

EXAMPLE 18

(2SR,12bSR)-spiro(1,3,4,6,7,12b-hexahydrobenzo[b]furo[2,3-a]quinolizin)-2,5'-oxazolidin-2'-one Step A: Preparation of (2SR,12bSR)-spiro(1,3,4,6,7,12b-hexahydrobenzo[b]furo[2,3-a]quinolizin)-2,2'-oxirane In a 50 ml 3 neck flask 0.053 g (1.1 mmol) sodium hydride as a 50% oil dispersion was washed three times with toluene under nitrogen. The resulting solid was then slurried in 10 ml dry DMF and cooled to 0° C. To this was added 0.25 g (1.1 mmol) trimethylsulfoxonium iodide. After stirring for 20 minutes, 0.241 g (1 mmol) of 1,3,4,6,7,12b-hexahydrobenzo[b]furo[2,3-a]quinolizin-2-one in 4 ml dry DMF was added dropwise. Stirring was continued for 10 minutes, after which the reaction was poured into 100 ml H₂O and extracted with 4×20 ml ethyl acetate. The combined organic extracts were washed with 25 ml brine, dried (Na₂SO₄) and the solvent was removed to obtain 0.25 g (98%) of 2SR,12bSR-spiro-(1,3,4,6,7,12b-hexahydrobenzo[b]furo[2,3-a]quinolizin)-2,2'-oxirane as a yellow solid which was recrystallized from ether/pet. ether; m.p. 109°–110° C.

Step B: Preparation of (2SR,12bSR)-2-aminomethyl-2-hydroxy-1,3,4,6,7,12b-hexahydrobenzo[b]furo[2,3-a]quinolizine Into a pressure bottle was placed 0.19 (0.4 mmol) (2SR,12bSR)-spiro-(1,3,4,6,7,12b-hexahydrobenzo[b]furo[2,3-a]quinolizin)-2,2'-oxirane dissolved in 10 ml absolute ethanol. After cooling the vessel to −78° C. using a dry ice/acetone bath, 10 ml ammonia was condensed into the bottle. The bottle was sealed, warmed to room temperature and allowed to stir for 48 hours after which the pressure was released and the solvent removed in vacuo. Subsequent spinning disc chromatography (5% methanol/chloroform saturated with ammonia) yielded 0.071 g. (83%) of (2SR,12bSR)-2-aminomethyl-2-hydroxy-1,3,4,6,7,12b-hexahydrobenzo[b]furo[2,3-a]quinolizine which was recrystallized from hexane/ethyl acetate; m.p. 155°–157° C.

Step C: Preparation of (2SR,12bSR)-spiro(1,3,4,6,7,12b-hexahydrobenzo[b]furo[2,3-a]quinolizin)-2,5'-oxazolidin-2'-one In a 50 ml flask, 0.093 g (0.34 mmol) (2SR,12bSR)-2-aminomethyl-2-hydroxy-1,3,4,6,7,12b-hexahydrobenzo[b]furo[2,3-a]quinolizine in 20 ml toluene was placed, and to this was added 0.102 g (0.62 mmol) 1,1'-carbonyldiimidazole. After refluxing for 1 hour, the reaction was cooled and washed with 3×10 ml H₂O, 10 ml brine, dried (Na₂SO₄) and the solvent removed to give 0.096 g (95%) (2SR,12bSR)-spiro-(1,3,4,6,7,12b-hexahydrobenzo[b]furo[2,3-a]quinolizin)-2,5'-oxazolidin-2'-one which was dissolved in 50 ml ethyl acetate. Ethanolic HCl was then added dropwise to give a white hydrochloride hemihydrate salt which was recrystallized from ethyl acetate, m.p. 280° C. (dec.).

EXAMPLE 19

(2RS,12bSR)-3'-Methyl-spiro(1,3,4,6,7,12b-hexahydrobenzo[b]furo[2,3-a]quinolizine)-2,4'-oxazolidin-2'-one Step A: Preparation of (2RS,12bSR)-2-Cyano-2-methylamino-1,3,4,6,7,12b-hexahydrobenzo[b]furo[2,3-a]quinolizine A mixture of 1,3,4,6,7,12b-hexahydrobenzo[b]furo[2,3-a]quinolizin-2-one (2.4 g, 9.9 mmole) and MgSO4 (250 mg) in dry tetrahydrofuran (600 ml) was saturated with methylamine at 0° C. Diethylcyanophosphonate (3.35 ml, 22.1 mmole) was added in one portion, and the mixture was left stoppered for 5 days. The reaction mixture was filtered; concentrated to dryness and the residue partitioned between ethyl acetate and H2O; the organic layer separated; washed with H2O, saturated NaCl solution; and dried (Na2SO4). Filtration and concentration gave crude subject compound (4.0 g) which was used immediately in the next step.

Step B: Preparaion of (2RS,12bSR)-Ethyl-2-methylamino-1,3,4,6,7,12b-hexahydrobenzo[b]furo[2,3-a]quinolizine-2-carboxylate Sulfuric acid (36N) (30 ml) was added to a solution of (2RS,12bSR)-2-cyano-2-methylamino-1,3,4,6,7,12b-hexahydrobenzo[b]furo[2,3-a]quinolizine (3.2 g, 0.011 mole) in 95% ethanol (30 ml) with cooling at 0° C. After heating at reflux for 3 hours, the reaction mixture was cooled to 0° C. treated with ice-H2O, basified with 20% NaOH solution and extracted with CH2Cl2. The organic layer was separated, washed with saturated NaCl solution and dried (Na2SO4). Filtration and concentration followed by flash chromatography provided 930 mg (26%) of the subject compound.

Step C: Preparation of (2RS,12bSR)-2-Hydroxymethyl-2-methylamino-1,3,4-6,7,12b-hexahydrobenzo[b]furo[2,3-a]quinolizine (2RS, 12bSR)-Ethyl-2-methylamino-1,3,4,6,7,12b-hexahydrobenzo[b]furo[2,3-a]quinolizin-2-carboxylate (940 mg, 2.86 mmole) in dry diethyl ether (20 ml) was added dropwise to a refluxing suspension of lithium aluminum hydride (108 mg, 2.86 mmole) in diethyl ether (20 ml) with stirring under N2. After heating at reflux for 2 hours, the reaction mixture was cooled to 0° C., the excess hydride was destroyed, and the mixture was left to stir for 16 hours. Filtration, followed by extraction of the salts with CH2Cl2 provided 560 mg (68%) of the title compound after chromatography.

Step D: Preparation of (2RS,12bSR)-3'-Methyl-spiro(1,3,4,6,7,12b-hexahydrobenzo[b]furo[2,3-a]quinolizine)-2,4'-oxazolidin-2'-one (2RS, 12bSR)-2-Hydroxymethyl-2-methylamino-1,3,4,6,7,12b-hexahydro-2H-benzo[b]furo[2,3-a]quinolizine (200 mg, 0.7 mmole) and 1,1'-carbonyldiimidazole (222 mg, 1.37 mmole) in toluene (120 ml) were stirred at ambient temperature for 18 hours. Water was added, the organic layer separated, extracted with saturated NaCl solution, dried (Na2SO4), then filtered and concentrated to give the title compound. Treatment with ethanolic HCl provided the hydrochloride salt (184 mg, 86.7%), m.p. 265°–267° C.

Anal. for C18H20N2O3.HCl 0.5 H2O: Calc'd: C, 60.41; H, 6.21; N, 7.83. Found: C, 60.42; H, 6.05; N, 7.72.

EXAMPLE 20

(2RS,12bSR)-1',3'-dimethyl-spiro(1,3,4,6,7,12b-hexahydrobenzo[b]furo[2,3-a]quinolizine)-2,4'-imidazolidin-2',5'-dione Methyl isocyanate (19 mg, 19.8 μl, 0.34 mmole) was added to a solution of (2RS, 12bSR)ethyl 2-methylamino-1,3,4,6,7,12b-hexahydro-2H-benzo[b]furo[2,3-a]quinolizine-2-carboxylate (100 mg, 0.30 mmole) in acetonitrile (10 ml) at ambient temperature with magnetic stirring under N2. After stirring for 18 hours the acetonitrile was removed, and the residue was dissolved in CHCl3, washed with H2O, saturated NaCl solution, and dried (Na2SO4). Filtration and concentration to dryness followed by conversion to the hydrochloride salt with ethanolic HCl gave 100 mg (87.4%) of (2RS,12bSR)-1',3'-dimethyl-spiro(1,3,4,6,7,12b-hexahydrobenzo[b]furo[2,3-a]quinolizine)-2,4'-imidazolin-2',5'-dione, m.p. 204°–206° C.

EXAMPLE 21

(2RS,12bSR)-spiro(1,3,4,6,7,12b-hexahydrobenzo[b]furo[2,3-a]quinolizin)-2,5'-oxazolidin-2'-one Step A: Preparation of (2RS,12bSR)-spiro(1,3,4,6,7,12b-hexahydrobenzo[b]furo[2,3-a]quinolizin)-2,2'-oxirane Into a mixture of n-butyllitium (1.6M/hexane, 3.5 ml) and (CH3)2S+CH3I− (1.23 g) in THF (25 ml), 1,3,4,6,7,12b-hexahydrobenzo[b]furo[2,3-a]quinolizin-2-one (400 mg) in THF (5 ml) was added at −5° C. with stirring under N2 gas. The mixture was stirred at 0° C. for 30 minutes and then at room temperature overnight. To the mixture, were added ethyl acetate and water with vigorous stirring and then an insoluble solid was filtered off. The ethyl acetate layer was separated, washed with H2O and dried over MgSO4. Evaporation of the ethyl acetate gave a yellow oil which was subjected to silica-gel column chromatography to give the oxirane which was recrystallized from a mixture of ether-petroleum ether to give yellow prisms; yield 70 mg; m.p. 108°–109° C.

Step B: Preparation of (2RS,12bSR)-2-aminomethyl-2-hydroxy-1,3,4,6,7,12b-hexahydrobenzo[b]furo[2,3-a]quinolizine An alcohol solution (15 ml) of the oxirane (170 mg) was taken into a pressure bottle and cooled in dry ice-acetone. After adding liquid NH3 (15 ml) to the ethanol solution, the mixture was left for 3 weeks with stirring. Evaporation of the ethanol gave a crude oil of the amino alcohol, (190 mg.)

Step C: Preparation of (2RS,12bSR)-spiro(1,3,4,6,7,12b-hexahydrobenzo[b]furo[2,3-a]quinolizin) 2,5'-oxazolidin-2'-one The amino alcohol from Step B (crude 180 mg) and 1,1'-carbonyldiimidazole (225 mg) were mixed in toluene (60 ml) under N2 gas and stirred overnight at room temperature. Water (5 ml) was added to the reaction mixture and it was stirred for 20 minutes. The toluene layer was separated and the water layer was washed with ethyl acetate. The organic layers were combined and washed with brine and water and dried over K2CO3. Evaporation gave a brown oil which was purified on chromatotron (a spinning thin layer chromatographic apparatus from Harrison Research, California) to give the oxazolidone. The oxazolidone was transformed into the HCl salt and recrytallized from ethanol-ether; yield 20 mg; m.p. 270° C. (dec.).

EXAMPLE 22

(2RS,12bSR)-3'-methyl-spiro-(1,3,4,6,7,12b-hexahydrobenzo[b]furo[2,3-a]quinolizin-2,5'-oxazolidin-2'-one Employing the procedure substantially as described in Example 3, but substituting for the (2SR,12bRS)-3'-methyl-spiro(1,3,4,6,7,12b-hexahydrobenzo[b]furo[2,3-a]quinolizin)-2,4'-imidazolidin-2'-one used therein, an equimolar amount of the spiro-oxazolidin-2-one from Example 21, the subject compound is produced in comparable yield.

EXAMPLE 23

(2RS,12bSR)-spiro-(1,3,4,6,7,12b-hexahydrobenzo[b]furo[2,3-a]quinolizine)-2,5'-pyrazolidin-3'-one Step A: Preparation of (E,Z)-2-Carboethoxymethylidine-1,3,4,6,7,12b-hexahydrobenzo[b]furo [2,3-a]quinolizine To a 3 necked 250 ml round bottomed flask with a stirring bar, argon inlet, thermometer and septum was added 8.11 g of a 28.6% suspension of potassium hydride in mineral oil. The oil was removed with two washings of hexane. To the oil free potassium hydride was added 25 ml of THF and the mixture was cooled to 0° C. A solution of triethylphosphonoacetate (12.98 g) in 15 ml of THF was added dropwise over 15 minutes. To this solution was added a solution of 3.00 g of 1,3,4,6,7,12b-hexahydrobenzo[b]furo[2,3-a]quinolizin-2-one in 25 ml of dry THF, dropwise over 15 minutes. This mixture was allowed to stir overnight at room temperature. The mixture was diluted wth 250 ml of ethyl acetate and was washed with water (3×200 ml) and brine (200 ml). Drying (magnesium sulfate), filtration and removal of the solvent in vacuo left an orange oil which was chromatographed on 300 g of silica gel with 30% ethyl acetate in hexanes as eluant. The chromatography provided two products: 650 mg of the faster eluting E isomer and 360 mg of the slower eluting Z isomer.

Step B: Preparation of (2RS,12bSR)-spiro-(1,3,4,6,7,12b-hexahydrobenzo[b]furo[2,3-a]quinolizine-2,5'-pyrazolidin-3'-one To a 15 ml round bottomed flask with a stirring bar, reflux condenser, and argon inlet was added 600 mg of either of the above unsaturated esters and 5 ml of anhydrous hydrazine. Five milliliters of dry benzene were added to dissolve the ester. The mixture was heated at reflux in an oil bath for 1 hour. The reaction mixture was cooled to room temperature and the crystals which had precipitated were collected on a frit. The crystals were washed with benzene, dried in vacuo and recrystallized from boiling methanol to provide 251 mg of the title pyrazolidinone; m.p. 286°–287° C.

EXAMPLE 24

(2RS,12bSR)-2'-methyl-spiro-(1,3,4,6,7,12b-hexahydrobenzo[b]furo[2,3-a]quinolizine)-2,5'-pyrazolidin-3'-one Step A: Preparation of (E,Z)-2-Carbomethoxymethylidine-1,3,4,6,7,12b-hexahydrobenzo[b]furo[2,3-a]-quinolizine To 200 ml round bottomed flask with a mechanical stirrer was added 2.84 g of 35% suspension of potassium hydride in mineral oil, under argon. The oil was removed with two washings of hexanes and 15 ml of dry THF was added. The stirring suspension was cooled to 0° C. and trimethylphosphonoacetate (4.53 g) was added, neat, dropwise. After this viscous mixture had stirred for 10 minutes a solution of 2.00 g of 1,3,4,6,7,12b-hexahydrobenzo[b]furo[2,3-a]quinolizin-2-one in 15 ml of dry THF was added with a syringe. The cooling bath was removed and the mixture was stirred overnight at room temperature. The reaction mixture was diluted with 200 ml of water and extracted with ethyl acetate (3×100 ml). The combined ethyl acetate extracts were washed with water and brine, dried over magnesium sulfate, filtered, and concentrated in vacuo. The crude product was chromatographed on 150 g of silica gel with 25% ethyl acetate in hexanes as eluant. This procedure provided 1.25 g of the faster eluting E isomer and 1.12 g of the slower eluting Z isomer. The free bases were converted to their HCL salts by the usual method: E-isomer; m.p. 218°–129° C.; Z-isomer; m.p. 220°–221° C.

The (12bR)- and (12bS)-enantiomers of the title compound were prepared by starting with the enantiomers of the quinolizin-2-one described in Example 1, Step F.

Step B: Preparation of (2RS,12bSR)-2'-Methyl-spiro-(1,3,4,6,7,12b-hexahydrobenzo[b]furo[2,3-a]quinolizine)-2,5'-pyrazolidin-3'-one dihydrochloride To a 25 ml round bottomed flask with stirring bar, reflux condenser and argon inlet was added 228 mg of the E-α,β-unsaturated ester from step A, 10 ml of dry THF, and 407 microliters of methylhydrazine. This solution was heated at reflux for 36 hours. The cooled reaction mixture was concentrated in vacuo and the residue was crystallized from ethyl acetate-hexanes. Recrystallization of this material from ethyl acetate-hexanes gave 127 mg of the free base; m.p. 180°–182° C. This material was converted into its dihydrochloride salt by dissolving it in boiling 2-propanol and adding two equivalents of ethanolic HCl. The crystals thus obtained were collected on a frit, washed with 2-propanol and dried to give 110 mg of the title compound; m.p. 270° C. (dec.).

EXAMPLE 25

(2RS,12bSR)-2'-Methyl-spiro-(1,3,4,6,7,12b-hexahydrobenzo[b]furo[2,3-a]-2,3'-isoxazolidin-5'-one To a 25 ml round bottomed flask with stirring bar, argon inlet and a reflux condenser was added 264 mg of the E -α,β-unsaturated ester from step A of Example 24, 417 mg of N-methylhydroxylamine hydrochloride and 829 mg of finely powdered potassium carbonate. To this mixture was added 10 ml of dry THF with a syringe. This suspension was heated at reflux with vigorous stirring for 24 hours. The reaction mixture was diluted with 100 ml of ethyl acetate and washed with water and brine. Drying (potassium carbonate), filtration and removal of the solvent in vacuo gave a yellow crystalline solid. Recrystallization of this material from boiling ethyl acetate-hexanes gave 146 mg of the title compound; m.p. 183°–185° C.

EXAMPLE 26

(2RS,12bSR)-1'-Methyl-spiro-(1,3,4,6,7,12b-hexahydrobenzo[b]furo[2,3-a]quinolizine)-2,4'-azetidin-2'-one To an argon filled Parr hydrogenation bottle was added 500 mg of (2RS,12bSR)-2'-methyl-spiro-(1,3,4,6,7,12b-hexahydrobenzo[b]furo[2,3-a]-2;3'-isoxazolidin-5'-one, 500 mg of 10% palladium on carbon, and 50 ml of methanol. This solution was hydrogenated on a Parr shaker at 50 psig and room temperature for 16 hours. The mixture was filtered through a celite pad and the catalyst was washed with a little methanol. The filtrates were combined and concentrated in vacuo. The residue was recrystallized from boiling 2-propanol and ethyl ether to obtain 500 mg of intermediate beta-amino acid used in the following reaction.

To a 200 ml round bottomed flask with a stirring bar and argon inlet was added the aforementioned beta-amino acid, 50 ml of dry methylene chloride, 279 microliters of triethylamine, and 345 mg of ethyl-(3-dimethylaminopropyl)carbodiimide hydrochloride. This solution was stirred under argon at room temperature for 70 hours. The solution was diluted with methylene chloride and washed with water and brine. Drying (magnesium sulfate), filtration and removal of the solvent in vacuo gave 442 mg of a yellow oil. This oil was chromatographed on 30 g of silica gel with 3% methanol in chloroform as eluant. Trituration of the oil obtained from the chromatography with 1:1 ethyl acetate-hexanes gave 126 mg of light yellow crystals of the title compound; m.p. 173°–175° C.

EXAMPLE 27

(2RS,12bSR)-1′,3′-dimethyl-spiro(1,3,4,6,7,12b-hexahydrobenzo[b]furo[2,3-a]quinolizin)-2,4′-(5′,6′-dihydro-1′H-pyrimidin-2′(3′H)-one, and (2SR,12bSR)-1′,3′-dimethyl-spiro-(1,3,4,6,7,12b-hexahydrobenzo[b]furo[2,3-a]quinolizin)-2,4′-(5′,6′-dihydro-1′H-pyrimidin-2′(3′H)-one)

Step A: Preparation of (2RS,12bSR)-N-methyl-(2-methylamino-1,3,4,6,7,12b-hexahydrobenzo[b]furo[2,3-a]quinolizin-2-yl)acetamide, and (2SR,12bSR)-N-methyl-(2-methylamino-1,3,4,6,7,12b-hexahydrobenzo[b]furo[2,3a]quinolizin-2-yl)acetamide Into a pressure bottle was placed 2.8 g (9.4 mmol) (E,Z)-2-carbomethoxymethylidine-1,3,4,6,7,12b-hexahydrobenzo[b]furo[1,2-a]quinolizine in 20 ml ethanol and the solution was cooled to −78° C. with a dry ice/acetone bath. Methylamine (20 ml) was condensed into the vessel which was then sealed and allowed to stir at room temperature for 7 days. The pressure was released and the solvent removed in vacuo to yield 3.0 g (97%) (2RS,12bSR)-N-methyl-(2-methylamino-1,3,4,6,7,12b-hexahydrobenzo[b]furo[2,3-a]quinolizin-2-yl)acetamide as a yellow oil.

The (12bR)- and (12bS)-enantiomers of the (2RS,12bSR)-title compounds were prepared by starting with the enantiomers of the carbomethoxymethylidene compound described in Example 24, Step A.

In a similar manner, 8.6 g (E,Z)-2-carbomethoxymethylidine-1,3,4,6,7,12b-hexahydrobenzo[b]furo[2,3-a]quinolizine was reacted in a pressure vessel at 100° C. for 18 hours in neat methylamine. Half of the crude reaction mixture (5 g) was subjected to medium pressure column chromatography (20% methanol/chloroform saturated with ammonia) to give 2.0 g (2RS,12bSR)-N-methyl-N-(2-methylamino-1,3,4,6,7,12b-hexahydrobenzo[b]furo[2,3-a]quinolizin-2-yl) acetamide as a yellow oil and 0.7 g of (2SR,12bSR)-N-methyl-N-(2-methylamino-1,3,4,6,7,12b-hexahydrobenzo[b]furo[2,3-a]quinolizin-2-yl)acetamide.

Step B: Preparation of (2SR,12bSR)-2-methylamino-2-(2′-methylaminoethyl)-1,3,4,6,7,12b-hexahydrobenzo[b]furo[2,3-a]quinolizine, and (2RS,12bSR)-2-methylamino-2-(2′-methylamino ethyl)-1,3,4,6,7,12b-hexahydrobenzo[b]furo[2,3-a]quinolizine Into a 500 ml flame dried flask was placed 10.8 ml (36.7 mmol) 3.4M sodium bis(2-methoxyethoxy) aluminum hydride in toluene and 150 ml dry THF. After heating to reflux, 3.0 gr. (9.1 mmol) (2RS,12bSR)-N-methyl-N-(2-methylamino-1,3,4,6,7,12b-hexahydrobenzo[b]furo[2,3-a]quinolizin-2-yl)acetamide in 50 ml dry THF was added dropwise over a 10 minute period. Refluxing was continued for 3 hours after which time the reaction was cooled and quenched by the dropwise addition of a saturated sodium potassium tartrate solution. The solvent was removed and the residue partitioned between H₂O/chloroform. The organic layer was separated, washed with 50 ml brine, dried (Na₂SO₄) and the solvent evaporated. Medium pressure column chromatography (10% methanol/chloroform saturated with ammonia gave 1.6 g (56%) (2RS,12bSR)-2-methylamino-2-(2′-methylaminoethyl)-1,3,4,6,7,12b-hexahydrobenzo[b]furo[2,3-a]quinolizine as a yellow oil.

Similarly prepared are the enantiomers of the title compound from enantiomeric acetamides from Step A.

Similarly, 0.186 g (0.57 mmol) (2SR,12bSR)-N-methyl-N-(2-methylamino-1,3,4,6,7,12b-hexahydrobenzo[b]furo[2,3-a]quinolizin-2-yl)acetamide was reduced using 0.67 ml (2.28 mmol) 3.4M sodium bis (2-methoxyethoxy)aluminum hydride to yield 0.082 g (48%) (2SR,12bSR)-2-methylamino-2-(2′-methylamino ethyl)-1,3,4,6,7,12b-hexahydrobenzo[b]furo[2,3-a]quinolizine as a yellow oil.

Step C: Preparation of (2RS,12bSR)-1′,3′-dimethyl-spiro(1,3,4,6,7,12b-hexahydrobenzo[b]furo[2,3-a]quinolizin)-2,4′-(5′,6′-dihydro-1′H-pyrimidin-2′(3′H)-one), and (2SR,12bSR)-1′,3′-dimethyl-spiro(1,3,4,6,7,12b-hexahydrobenzo[b]furo[2,3-a]quinolizin)-2,4′-(5′,6′-dihydro-1′H-pyrimidin-2′(3′H)-one)

Into a 300 ml flask was placed 1 g (3.2 mmol) (2RS,12bSR)-2-methylamino-2-(2′-methylaminoethyl)-1,3,4,6,7,12b-hexahydrobenzo[b]furo[2,3-a]quinolizine in 100 ml toluene followed by 0.95 g. (5.9 mmol) 1,1′-carbonyldiimidazole. The reaction was heated to 50° C. for 5 hours, after which time the reaction was treated as previously described to give 0.85 g (78%) (2SR,12bSR)-1′,3′-dimethyl-spiro(1,3,4,6,7,12b-hexahydrobenzo[b]furo[2,3-a]quinolizin)-2,4′-(5′,6′-dihydro-1′H-pyrimidin-2′(3′H)-one) which was dissolved in ethyl acetate and ethanolic HCl was added to give the hydrochloride sesquihydrate as a white crystalline salt; m.p. 171°–173° C.

Employing the above procedure but starting with the enantiomers of the diamine from Step B, there were produced the (2S,12bS)- and (2R,12bR)-enantiomers of the title compound with $[\alpha]_D -6.2°$ (C=0.0016 g/ml CH₃OH) and $[\alpha]_D +6.2°$ (C=0.0016 g/ml CH₃OH) respectively, m.p. 283°–285° C.

In a similar manner, 0.078 g (0.25 mmol) (2SR,12bSR)-2-methylamino-2-(2′-methylaminoethyl)-1,3,4,6,7,12b-hexahydrobenzo[b]furo[2,3-a]quinolizine was reacted with 0.078 gr. (0.5 mmol) 1,1′-carbonyldiimidazole to give 0.02 g (24%) (2RS,12bSR)-1′,3′-dimethyl-spiro(1,3,4,6,7,12b-hexahydrobenzo[b]furo [2,3-a]quinolizin]-2,4′-(5′,6′-dihydro-1′H-pyrimidin-2′(3′H)-one) after heating for 24 hours at 50° C. as a yellow oil.

EXAMPLE 28

(2RS,12bSR)-1′,3′-dimethyl-spiro(1,3,4,6,7,12b-hexahydrobenzo[b]-furo[2,3-a]quinolizin)-2,4′-(5′H-pyrimidin-2′(3′H),6′(1′H)-dione Into a dry 50 ml 3 neck flask was placed 0.164 g (0.5 mmol) (2RS,12bSR)-2-methylamino-2-(2-N-methyl acetamido)-1,3,4,6,7,12b-hexahydrobenzo[b]furo[2,3-a]quinolizine in 10 ml dry THF and the solution was cooled to −78° C. using a dry ice/acetone bath. To this was added 0.462 ml (0.5 mmol) 1.3M n-butyl lithium in hexane and the mixture was stirred at −78° C. for 15 minutes. The solution was then transferred via cannula to a solution of 0.081 g (0.5 mmol) 1,1′-carbonyldiimidazole in 10 ml THF at 0° C. and the mixture stirred 18 hours at room temperature. The solvent was removed and the residue partitioned between ethyl acetate/H₂O. The layers were separated and the organic fraction washed with 3×50 ml H₂O, 50 ml brine, dried (MgSO₄) and the solvent removed. Spinning disc chromatography yielded 0.057 g (32%) (2RS,12bSR)-1',3'-dimethylspiro(1,3,4,6,7,12b-hexahydrobenzo[b]furo[2,3-a]quinolizin)-2,4'-(5'H-pyrimidin-2'(3'H),6'(1'H)-dione) as a yellow oil which was dissolved in ethyl acetate and ethanolic HCl added. Dilution with ether gave the hydrochloride hydrate salt as a white solid; m.p. 201°–203° C.

EXAMPLE 29

(2SR,12bSR)-3'-Methyl-spiro(1,3,4,6,7,12b-hexahydrobenzo[b]furo[2,3-a]quinolizine)-2,4'-(3',4',5',6'-tetrahydro-1',3'-oxazin-2'-one)

To a 200 ml round bottomed flask with stirring bar was added 760 mg of (2RS,12bSR)-2'-methyl-spiro-(1,3,4,6,7,12b-hexahydrobenzo[b]furo [2,3-a]quinolizine)-2,3'-isoxazolidin-5'-one, 20 ml of dry THF and 9.7 ml of 1M borane-THF complex. This solution was heated at reflux under argon for 20 hours. The cooled reaction mixture was quenched with 5% aqueous HCl and partitioned between 200 ml of 5% HCl and 500 ml of ether. The layers were separated and the aqueous phase was made basic with 10N sodium hydroxide. This solution was extracted with chloroform (3×50 ml) and the combined chloroform extracts were washed with brine and dried over anhydrous potassium carbonate. Filtration and removal of the solvent in vacuo gave 430 mg of crude intermediate amino-alcohol. This amino-alcohol was chromatographed on 20 g of silica gel with 0.1% methanol in ammonia saturated chloroform as eluant. There was obtained 144 mg of pure intermediate aminoalcohol as a colorless foam.

To a 100 ml round bottomed flask containing 100 mg of the aforementioned amino-alcohol was added 3 ml of chloroform and 406 ml of 1,1'-carbonyldiimidazole. This mixture was stirred under argon at room temperature for 48 hours. The reaction mixture was diluted with ethyl acetate and washed with water and brine. Drying (potassium carbonate), filtration and removal of the solvent in vacuo gave an oil which was chromatographed on 5 g of silica gel with 25% ethyl acetate in hexanes as eluant. The oil obtained from this chromatography was rechromatographed on 5 g of silica gel with 2% methanol in chloroform as eluant. The crystalline product thus obtained was recrystallized from a 1:1 mixture of boiling ethyl acetate-hexanes to give 69.8 mg of the title compound as white crystals, m.p. 216°–218° C.

EXAMPLE 30

(2RS,12bSR)-4'-Methyl-spiro(1,3,4,6,7,12b-hexahydro benzo[b]furo(2,3-a]quinolizine-2,5'-(2',4',5',6'-tetrahydro-1',4'-oxazin-3'-one)

Step A: Preparation of (2RS,12bSR) 2-chloroacetoxymethyl-2-(N-methyl-2-chloroacetamido)-1,3,4,6,7,12b-hexahydro-2H-benzo[b]furo [2,3-a]quinolizine Chloroacetyl chloride (35 mg, 0.314 mmol) was added dropwise to a solution of (2RS,12bSR)-2-hydroxymethyl-2-methylamino-1,3,4,6,7,12bα-hexahydrobenzo[b]furo[2,3-a]quinolizine (40 mg, 0.14 mmole) and triethylamine (43 μl, 0.314 mmol) in CH₂Cl (10 ml) with stirring at 0° C., under N₂. After stirring at ambient temperature for 18 hours, the reaction mixture was treated with H₂O, the organic layer separated, washed with saturated NaCl solution, dried (Na₂SO₄) and concentrated to dryness to give the bisacylated material, 58 mg (95%).

Step B: Preparation of (2RS,12bSR)-4'-Methyl-spiro-(1,3,4,6,7,12b-hexahydrobenzo[b]furo[2,3-a]quinolizine)-2,5'-(2',4',5',6'-tetrahydro-1',4'-oxazin-3'-one)

The product from Step A (58 mg, 0.13 mmol) was dissolved in toluene (15 ml) and treated with a finely ground mixture of KOH and neutral alumina (1:1) (115 mg) with stirring at ambient temperature. After 2 hours the reaction mixture was filtered, the filtrate washed with H₂O, saturated NaCl solution, and dried (Na₂SO₄). Flash chromatography provided 33 mg (75%) of (2RS,12bSR)-4'-Methyl-spiro-(1,3,4,6,7,12b-hexahydrobenzo[b]furo[2,3-a]quinolizine)-2,5'-(2',4',5',6'-tetrahydro-1',4'-oxazin-3'-one), m.p. 159°–63° C.

Anal. for C₁₉H₂₂N₂O₃.

EXAMPLE 31

(2RS,12bSR)-4'-Methyl-spiro(1,3,4,6,7,12b-hexahydrobenzo[b]furo[2,3-a]quinolizine)-2,5'-piperazin-2',3'-dione (2RS,12bSR)-2-Aminomethyl-2-methylamino-1,3,4,6,7,12b-hexahydrobenzo[b]furo[2,3-a]quinolizine (310 mg, 1.08 mmol) and diethyl oxalate (200 μl, 1.48 mmol) in toluene (50 ml) were heated at reflux for 27 hours, then concentrated to dryness, and the residue was chromatographed to give 60 mg (16%) of 2RS,12bSR)-4'-methyl-spiro(1,3,4,6,7,12b-hexahydrobenzo[b]furo[2,3-a]quinolizine)-2,5'-piperazin-2',3'-dione, m.p. 218°–220° C.

Anal. for C₁₉H₂₁N₃O₃·¼H₂O: Calc'd: C, 66.36; H, 6.30; N, 12.22. Found: C, 66.43; H, 6.51; N, 12.01.

EXAMPLE 32

Preparation of (2RS,12bSR)-4'-Methyl-spiro-(1,3,4,6,7,12b-hexahydrobenzo[b]furo[2,3-a]quinolizine)-2,5'-piperazin-3'-one Step A: Preparation of (2RS,12bSR)-2-Methylamino-1,3,4,6,7,12b-hexahydro-2-trifluoroacetamidomethyl-benzo[b]furo[2,3-a]quinolizine Trifluoroacetic anhydride (1.84 ml, 13 mmol) dissolved in CH₂Cl₂ (5 ml) was added dropwise to a solution of (2RS,12bSR)-2-aminomethylo-2-methylamino-1,3,4,6,7,12b-hexahydrobenzo[b]furo[2,3-a]quinolizine (920 mg, 3.2 mmol) in CH₂Cl₂ (50 ml) with stirring at 0° C. under N₂. The reaction mixture was concentrated to dryness, and the residue was treated with H₂O and extracted with CH₂Cl. The aqueous acidic layer was basified with saturated NaHCO₃ solution, extracted with CH₂Cl₂, the extract was washed with saturated NaCl solution and dried (MgSO₄). Filtration and concentration to dryness provided 140 mg (12%) of the monoacylated amine.

Step B: Preparation of (2RS,12bSR)-N-Methyl-N-(1,3,4,6,7,12b-hexahydro-2-trifluoroacetamidomethyl-benzo[b]furo[2,3-a]quinolizin-2-yl)chloroacetamide Chloroacetyl chloride (31.8 μl, 0.4 mmol) in CH₂Cl₂ (5 ml) was added to a solution of the product from Step A (140 mg, 0.37 mmol) and triethylamine (55.7 μl, 0.4 mmol) in CH₂Cl₂ (20 ml) with stirring at 0° C. under N₂. After stirring at ambient temperature for 2 hours, the reaction mixture was treated with ice-H₂O, the organic layer was separated, washed with saturated NaCl solution and dried (MgSO₄). Filtration and concentration to dryness gave 80 mg (47%) of the diacyl product.

Step C: Preparation of (2RS,12bSR)-4'-Methyl-spiro (1,3,4,6,7,12b-hexahydro-2H-benzofuro[2,3-a]quinolizine)-2,5'-piperazin-3'-one The product from Step B (80 mg, 0.17 mmole) and KOH (2 pellets) were stirred in methanol (20 ml) at ambient temperature for 2 hours. The reaction mixture was concentrated to dryness, then partitioned between $CH_2Cl_2$ and $H_2O$. The organic layer was separated, washed with saturated NaCl solution and dried ($MgSO_4$). Filtration and concentration to dryness provided 30 mg (55%) of (2RS,12bSR)-4'-Methyl-spiro(1,3,4,6,7,12b-hexahydro-2H-benzofuro[2,3-a]quinolizine)-2,5'-piperazin-3'-one after chromatography. Treatment with ethanolic HCl gave the hydrochloride salt, m.p. 225°–230° C.

Anal. for $C_{19}H_{23}N_3O_2 \cdot 2HCl \cdot \frac{1}{2}H_2O$: Calc'd: C, 56.03; H, 6.43; N, 10.32. Found: C, 55.94; H, 6.43; N, 9.94.

EXAMPLE 33

(2SR,11bSR)-3,4,5',6',7,11b-octahydro-1',3'-dimethyl-spiro(2H-benzo[a]quinolizine)-2,4'(1'H-pyrimidin-2'-(3'H)-one),monohydrochloride Step A: Preparation of (E,Z) 2-Carbomethoxymethylidene-1,3,4,-6,7,11b-hexahydrobenzo[a]quinolizine To a 500 ml 3-necked round bottomed flask with a stirring bar was added 25% potassium hydride-oil suspension (14.68 g, 91.52 mmol) under argon. The oil was removed by washing with hexane. The oil free potassium hydride was suspended in 100 ml of dry THF and was cooled to 0° C. Trimethylphosphonoacetate (16.67 g, 91.52 mmol) in 50 ml of THF was added to the well stirred potassium hydride, dropwise over 30 minutes. When the addition was complete the mixture was allowed to stir for an additional 15 minutes then a solution of 1,2,4,6,7,11b-hexahydrobenzo[a]quinolizin-2-one (6.14 g, 30.51 mmol) in 50 ml of THF was added dropwise, over 15 minutes. The cooling bath was allowed to expire and the mixture was stirred overnight at room temperature. The reaction mixture was diluted with ethyl acetate and washed with water (3×) and brine. Drying ($MgSO_4$), filtration, and removal of the solvent in vacuo gave 7.18 g (91%) of a 1:1 mixture of (E:Z) 2-carbomethoxymethylidine-1,3,4,6,7,11b-hexahydrobenzo[a]quinolizine.

Step B: Preparation of (2RS,11bSR)-N-methyl-2-(2-methylamino-1,3,4,6,7,11b-hexahydrobenzo[a]quinolizin-2-yl)acetamide To a 125 ml pressure vessel was added a solution of (E:Z) 2-carbomethoxymethylidine-1,3,4,6,7,11b-hexahydrobenzo[a]quinolizine (7.18 g 27.90 mmol) in 25 ml of absolute ethanol. This solution was cooled to −78° C. and 25 ml of methylamine was condensed into the mixture. A stirring bar was added, the vessel sealed, and the mixture was stirred at room temperature for 96 hours.

The vessel was vented and the contents were concentrated in vacuo. Chromatography of the residue on 200 g of silica gel using 2.5% methanol in ammonia saturated chloroform as eluant gave 5.04 g (63%) of (2RS,11bSR)-N-methyl-2-(2-methylamino-1,3,4,6,7,11b-hexahydrobenzo[a]quinolizin-2-yl)acetamide as a yellowish oil.

Step C: Preparation of (2RS,11bSR)-2-methylamino-2-(2-methylaminoethyl)-1,3,4,6,7,11b-hexahydrobenzo[a]quinolizine To a 500 ml round bottomed flask with stirring bar, refluxed condenser, dropping funnel and argon inlet was added a solution of sodium bis(2-methoxyethoxy)aluminum hydride (20.63 ml of a 3.4M solution in toluene) and 100 ml of dry THF. This solution was heated at reflux and a solution of the acetamide (5.04 g, 17.54 mmol) from Step B in 100 ml of dry THF was added dropwise over 45 minutes. When the addition was complete the mixture was heated at reflux for 2 hours. The reaction mixture was chilled in an ice bath and quenched with 100 ml of saturated aqueous potassium sodium tartrate solution. The resulting mixture was diluted with ethyl acetate (300 ml) and the layers were separated. The organic phase was washed with an additional 200 ml of tartrate solution and 200 ml of brine. Drying ($K_2CO_3$), filtration and removal of the solvent in vacuo left 4.90 g of (2RS,11bSR)-2-methylamino-2-(2-methylaminoethyl)-1,3,4,6,7,11b-hexahydrobenzo[a]quinolizine as an oil.

Step D: Preparation of (2RS,11bSR)-1,3,4,5',6,6'7,11b-octahydro-1',3'-dimethyl-spiro(2H-benzo[a]-quinolizine)-2,4'(1'H-pyrimidin-2'(3'H)-one)monohydrochloride To a 200 ml round bottomed flask with stirring bar and argon inlet was added (2RS,11bSR)-2-methylamino-2-(2-methylaminoethyl)-1,3,4,6,7,11b-hexahydrobenzo[a]quinolizine (3.57 g, 13.06 mmol), 50 ml of dry toluene and 1,1'-carbonyldiimidazole (3.17 g, 19.59 mmol). This solution was heated at 50° C. for 20 hours. The cooled mixture was diluted with ethylacetate and washed with water (3×100 ml) and brine (200 ml). Drying ($MgSO_4$), filtration and removal of the solvent in vacuo left an oil which was chromatographed on 150 g of silica gel using ammonia saturated chloroform as eluant. The purified free base obtained from the chromatography was crystallized as its monohydrochloride salt from ethanolic HCl. Vacuum drying at 80° C. for 24 hours gave 2.36 g of the title compound, m.p. 275° C., (decomp.).

EXAMPLE 34

(2SR,12bSR)-1'-Methyl-spiro(1,3,4,6,7,12b-hexahydrobenzo[b]furo[2,3-a]quinolizin-2,4'-(tetrahydro-(1'H)pyrimidin-2'-one)

Step A: Preparation of 2RS,12bSR)-methyl-(2-amino-1,3,4,6,7,12b-hexahydrobenzo[b]furo[2,3-a]quinolizin-2-yl)acetate A mixture of 0.149 g (0.5 mmol) of (E,Z)-2-carbomethoxymethylidine-1,3,4,6,7,12b-hexahydrobenzo[b]furo[2,3-a]quinolizine and 10 ml absolute ethanol were cooled to −78° C. in a pressure vessel. Dry ammonia gas (20 ml) was condensed into the flask, which was then sealed, warmed to ambient temperature and allowed to stir for 18 hours. The pressure was released and the solvent removed in vacuo to give 0.073 g (46%) (2RS,12bSR)-methyl (2-amino-1,3,4,6,7,12b-hexahydrobenzo[b]furo[2,3-a]quinolizin-2-yl)acetate as a yellow oil after purification by spinning disc chromatography (2% methanol/ammonia saturated chloroform).

Step B: Preparation of (2RS, 12bSR)-N-methyl-(2-amino-1,3,4,6,7,12b-hexahydrobenzo[b]furo[2,3-a]quinolizin-2-yl)acetamide A mixture of 0.3 g (0.95 mmol) of (2RS, 12bSR)-methyl-(2-amino-1,3,4,6,7,12b-hexahydrobenzo[b]furo[2,3-a]quinolizin-2-yl)acetate and 25 ml absolute ethanol were reacted employing the procedure substantially as described in Example 27, Step A to obtain 0.25 g (84%) of (2RS, 12bSR-N-methyl-(2-amino-1,3,4,6,7,12b-hexahydrobenzo[b]furo[2,3-a]quinolizin-2-yl)acetamide as a yellow oil.

Step C: Preparation of (2RS, 12bSR)-2-amino-2-(2-methylaminoethyl)-1,3,4,6,7,12b-hexahydrobenzo[b]furo[2,3-a]quinolizine A mixture of 0.94 ml (3.26 mmol) 3.4M sodium bis (2-methoxyethoxy)aluminum hydride and 0.25 g (0.8 mmol) of (2RS,12bSR)-N-methyl-(2-amino-1,3,4,6,7,12b-hexahydrobenzo[b]furo[2,3-a]quinolizin-2-yl)acetamide were reacted employing the procedure substantially as described in Example 27, Step B to yield 0.146 g (61%) of (2RS,12bSR-2-amino-2-(2'-methylaminoethyl)-1,3,4,6,7,12b-hexahydrobenzo[b]furo[2,3-a]quinolizine as a yellow oil after purification by spinning disc chromatography (ammonia saturated chloroform).

Step D: Preparation of (2SR,12bSR)-1,3,4,5'6,6',7,12b-octahydro-1'-methyl-spiro(2H-benzofuro[2,3-a]quinolizine-2,4'(1'H)-pyrimidin)-2'-(3'H)-one A mixture of 0.146 g (0.49 mmol) of (2RS,12bSR)-2-amino-2-(2'-methylaminoethyl)-1,3,4,6,7,12b-hexahydrobenzo[b]furo[2,3-a]quinolizine and 0.158 g (0.98 mmol) of 1,1'-carbonyldiimidazole in 25 ml dry toluene were reacted employing the procedure substantially as described in Example 27, Step C to give 0.052 g (28%) of (2SR,12bSR)-1,3,4,5',6,6',7,12b-octahydro-1'-methyl-spiro(2H-benzofuro[2,3-a]quinolizine)-2,4'(1'H-pyrimidin-2'(3'H)-one)hydrochloride monohydrate as a white solid; m.p. 190° C. (dec).

EXAMPLE 35

(2SR,12bSR)-1,3,4,5',6,6',7,12b-octahydro-3'-methyl-1'-(2-hydroxyethyl)-spiro(2H-benzofuro[2,3-a]quinolizine)-2,4'(1'H-pyrimidin-2'(3'H)-one)

Step A: Preparation of (2RS,12bSR)-methyl (2-methylamino-1,3,4,6,-7,12b-hexahydrobenzo[b]furo[2,3-a]quinolizin-2-yl)acetate Employing the procedure substantially as described in Example 27, Step A, but stirring for only 4 hours, 3 g (10 mmol) (E,Z)-2-carbomethoxymethylidine-1,3,4,6,7,12b-hexahydrobenzo[b]furo[2,3-a]quinolizine was reacted with 20 ml methylamine in 20ml ethanol to give 2.7 g (85%) of (2RS,12bSR)-methyl-(2-methylamino-1,3,4,6,7,12b-hexahydrobenzo[b]furo[2,3-a]quinolizin-2-yl)acetate as a yellow oil.

Step B: Preparation of (2RS,12bSR)-N-(2-propenyl)-2-(2-methylamino-1,3,4,6,7,12b-hexahydrobenzo[b]furo[2,3-a]quinolizin-2-yl)acetamide A mixture of 2.6 g (8 mmol) of (2RS,12bSR)methyl-2-(2-methylamino-1,3,4,6,7,12b-hexahydrobenzo[b]furo[2,3-a]quinolizin-2-yl)acetate, 50 ml allylamine and 50 ml absolute ethanol were refluxed for 3 days. The reaction was cooled and the solvent removed in vacuo to give 1.8 g (63.7%) of (2RS,12bSR)-N-(2-propenyl)-2-(2-methylamino-1,2,4,6,7,12b-hexahydrobenzo[b]furo[2,3-a]quinolizin-2-yl)acetamide as a yellow oil after medium pressure column chromatography (ammonia saturated chloroform).

Step C: Preparation of (2RS,12bSR)-2-methylamino-2-(2-(2-propenylamino)ethyl)-1,3,4,6,7,12b-hexahydrobenzo[b]furo[2,3-a]quinolizine Employing the procedure substantially as described in Example 27, Step B, 1.8 g (5 mmol) of (2RS,12bSR)-N-(2-propenyl)-2-(2-methylamino-1,3,4,6,7,12b-hexahydrobenzo[b]furo[2,3-a]quinolizin-2-yl)acetamide and 6 ml (20 mmol) of 3.4M sodium bis (2-methoxyethoxy)aluminum hydride were reacted to give 1.2 g (70.7%) of (2RS,12bSR)-2-methylamino-2-(2-(2-propenylamino)ethyl)-1,3,4,6,7,12b-hexahydrobenzo[b]furo[2,3-a]quinolizine as a yellow oil after medium pressure column chromatography (ammonia saturated chloroform).

Step D: Preparation of (2SR,12bSR)-1,3,4,5',6,6',7,12b-octahydro-1'-(2-propenyl)-3'-methylspiro(2H-benzofuro[2,3-a]quinolizin)-2,4'-(1'H-pyrimidin-2'(3'H)-one)

Employing the procedure substantially as described in Example 27, Step C, 1.2 g (3.5 mmol) of (2RS,12bSR)-2-methylamino-2-(2-(2 propenyl amino)ethyl)-1,3,4,6,7,12b-hexahydrobenzo[b]furo[2,3-a]quinolizine and 1.14 g (7 mmol) of 1,1'-carbonyldiimidazole were reacted to give 0.8 g (63%) of (2SR,12bSR)-1,3,4,5',6,6',7,12b-octahydro-1'-(2-propenyl)-3'-methyl-spiro(2H-benzofuro[2,3-a]quinolizin)-2,4'(1'H-pyrimidin-2'(3'H)-one) as a yellow waxy solid after purification by flask column chromatography, from which was made the hydrochloride dehydrate salt. m.p. 174°–176° C.

Step E: Preparation of (2SR,12bSR)-1,3,4,5',6,6'7,12b-octahydro-3'-methyl-1'-(2,3-dihydroxypropyl)-spiro(2H-benzofuro[2,3-a]quinolizine)-2,4'(1'H-pyrimidin-2'(3'H)-one)

Employing the procedure substantially as described in Example 36, Step E, a mixture of 0.1 g (0.27 mmol) of (2SR,12bSR)-1,3,4,5',6,6',7,12b-octahydro-1'-(2 propenyl)-3'-methyl-spiro(2H-benzofuro[2,3-a]quinolizin)-2,4'-(1'H-pyrimidin-2'(3'H)-one), 0.073 g (0.54 mmol) of 4-methylmorpholine-4-oxide monohydrate and 2 drops of osmium tetroxide (0.4M solution in THF) were reacted to give 0.06 g (55%) of (2SR,12bSR)-1,3,4,5',6,6',7,12b-octahydro-3'-methyl-1'-(2,3-dihydroxypropyl)-spiro(2H-benzofuro[2,3-a]quinolizine)-2,4'(1'H-pyrimidin-2'(3'H)-one) as a waxy solid after purification by flash column chromatography (ammonia saturated chloroform), from which was made the hydrochloride dihydrate salt. m.p. 175°–177° C. (dec).

Step F: Preparation of (2SR,12bSR)-1,3,4,5',6,6',7,12b-octahydro-3'-methyl-1'-(2-hydroxyethyl)spiro(2H-benzofuro[2,3-a]quinolizine)-2,4'-(1'H-pyrimidin-2'(3'H)-one)

A mixture of 0.125 g (0.31 mmol) of (2SR, 12bSR)-1,3,4,5',6,6',7,12b-octahydro-3'-methyl-1'-(2,3-dihydroxypropyl)-spiro(2H-benzofuro[2,3-a]quinolizine)-2,4'(1'H-pyrimidin-2'(3'H)-one) and 0.125 ml 20% NaOH were dissolved in 10 ml 95% ethanol and cooled to 0° C. To this solution was added 0.2 g (0.93 mmol) of sodium periodate dropwise in 5 ml H$_2$O. The reaction was allowed to stir for 2 hours at 0° C., then the solvent was removed and the residue was partitioned between water/chloroform. The layers were separated, the organics dried (MgSO$_4$) and the solvent removed to give the crude aldehyde which was immediately dissolved in 10 ml absolute ethanol and treated with a large excess (0.15 g) of sodium borohydride. After stirring 18 hours, the solvent was removed and the residue worked up to give 0.048 g (42%) of (2SR,12bSR)-1,3,4,5',6,6',7,12b-octahydro-3'-methyl-1'-(2-hydroxyethyl)-spiro(2H-benzofuro[2,3-a]quinolizine)-2,4'(1'H-pyrimidin-2'(3'H)-one) as a white crystalline solid m.p. 174°–176° C.

EXAMPLE 36

(2SR,12bSR)-1,3,4,5',6,6'7,12b-octahydro-1'-methyl-3'-(2-hydroxyethyl)-spiro(2H-benzofuro[2,3-a]quinolizine-2,4'(1'H)-pyrimidin)-2'(3'H)-one Step A: Preparation of (2RS,12bSR)-methyl-2-(2-(2-propenylamino)-1,3,4,6,7,12b-hexahydrobenzo[b]furo[2,3-a]quinolizin-2-yl)acetate A mixture of 0.148 g (0.5 mmol) of (E,Z)-2-carbomethoxymethylidine-1,3,4,6,7,12b-hexahydrobenzo[b]furo[2,3-a]quinolizin, 5ml of allylamine and 5 ml absolute ethanol were refluxed under a nitrogen atmosphere for 18 hours, after which the solvent was removed and the resulting residue purified by spinning disc chromatography (1:1 hexane/ammonia saturated chloroform) to give 0.063 g (36%) of (2SR,12bSR)-methyl-(2-(2-propenylamino)-1,3,4,6,7,12b-hexaydrobenzo[b]furo[2,3-a]quinolizin-2-yl)acetate as a yellow oil.

Step B: Preparation of (2RS,12bSR)-N-methyl-2-(2-(2-propenyl amino)-1,3,4,6,7,12b-hexahydrobenzo[b]furo[2,3-a]quinolizin-2-yl)acetamide A mixture of 0.86 g (2.4 mmol) of (2RS,12bSR-methyl-2-(2-(2-propenylamino)-1,3,4,6,7,12b-hexahydrobenzo[b]furo[2,3-a]quinolizin-2-yl)acetate and dry methylamine where reacted employing the procedure substantially as described in Example 27, Step A to give (2RS,12bSR)-N-methyl-2-(2-(2-propenylamino)-1,3,4,6,7,12b-hexahydrobenzo[b]furo[2,3-a]quinolizin-2-yl)acetamide (0.5 g, 58%) as a yellow oil after purification by medium pressure column chromatography (ammonia saturated chloroform).

Step C: Preparation of (2RS,12bSR)-2-(2-propenylamino)-2-(2-methylaminomethyl)-1,3,4,6,7,12b-hexahydrobenzo[b]furo[2,3-a]quinolizine A mixture of 1.66 ml (5.6 mmol) of 3.4M sodium bis(2-methoxyethoxy)aluminum hydride and 0.5 g (1.4 mmol) of (2RS,12bSR)-N-methyl-2-(2-(2-propenylamino)-1,3,4,6,7,12b-hexahydrobenzo[b]furo[2,3-a]quinolizin-2-yl)acetamide were reacted employing the procedure substantially as described in Example 27, Step B to yield 0.116 g (24%) of (2RS,12bSR)-2-(2-propenylamino)-2-(2-methylaminoethyl)-1,3,4,6,7,12b-hexahydrobenzo[b]furo[2,3-a]quinolizine as a yellow oil after purification by spinning disc chromatography (3% methanol/ammonia saturated chloroform).

Step D: Preparation of (2SR,12bSR)-1,3,4,5',6,6',7,12b-octahydro-1'-methyl-3'-(2-propenyl)-spiro(2H-benzofuro[2,3-a]quinolizin)-2,4'-(1'H-pyrimidin-2'(3'H)-one A mixture of 0.116 g (0.34 mmol) of (2RS,12bSR)-2-(2-propenylamino)-2-(2-methylaminoethyl)-1,3,4,6,7,12b-hexahydrobenzo[b]furo[2,3-a]quinolizine and 0.11 g (0.68 mmol) 1,1'-carbonyldiimidazole in 20 ml was reacted employing the procedure substantially as described in Example 27, Step C to get 0.063 g (51%) of (2RS,12bSR)-1,3,4,5',6,6',7,12b-octahydro-1'-methyl-3'-(2-propenyl)-spiro(2H-benzofuro[2,3-a]quinolizin)-2,4'(1'H-pyrimidin-2'(3'H)-one) after purification by spinning disc chromatography (ammonia saturated chloroform), from which was made the hydrochloride dihydrate salt, m.p. 173°–175° C. (dec).

Step E: Preparation of (2SR,12bSR)-1,3,4,5',6,6',7,12b-octahydro-1'-methyl-3'-(2,3-dihydroxypropyl)-spiro-(2H-benzofuro[2,3-a]quinolizine)-2,4'(1'H-pyrimidin-2'(3'H)-one)

A mixture of 0.1 g (0.27 mmol) of (2SR,12bSR)-1,3,4,5',6,6',7,12b-octahydro-1'-methyl-3'-(2-propenyl)-spiro(2H-benzofuro[2,3-a]quinolizine)-2,4'(1'H-pyrimidin-2'(3'H)-one) and 0.73 g (0.54 mmol) 4-methylmorpholine-4-oxide monohydrate were dissolved in 25 ml THF, and to this was added 2 drops of a 0.4M solution of osmium tetroxide in THF. The reaction was stirred 18 hours after which time it was poured into 50 ml water and extracted with 3×25 ml chloroform. The organic layer was dried (MgSO4) and the solvent removed to give 0.08 g (74.4%) of (2SR,12bSR-1,3,4,5',6,6',7,12b-octahydro-1'-methyl-3'-(2,3-dihydroxypropyl)-spiro(2H-benzofuro[2,3-a]quinolizine)-2,4'(1'H-pyrimidin-2'(3'H)-one) after flash column chromatography (ammonia saturated chloroform), from which was made the hydrochloride dehydrate salt. m.p. 175°–178° C.

Step F: Preparation of (2SR,12bSR)-1,3,4,5',6,6',7,12b-octahydro-3'-(2-hydroxyethyl)-1'-methyl-spiro(2H-benzofuro[2,3-a]quinolizine)-2,4'-(1'H)-pyrimidin-2'(3'H)-one)

A mixture of 0.05 g (0.12 mmol) of (2SR,12bSR)-1,3,4,5',6,6'7,12b-octahydro-1'-methyl-3'-(2,3-dihydroxypropyl)-spiro(2H-benzofuro[2,3-a]quinolizin)-2,4'-(1'H-pyrimidin-2'(3'H)-one), 0.079 g (0.36 mmol) of sodium periodate and 0.05 ml 20% NaOH are reacted followed by a large excess of sodium borohydride employing the procedure substantially as described in Example 35, Step F to give 0.026 g (58.6%) of (2SR,12bSR)-1,3,4,5',6,6',7,12b-octahydro-3'-(2-hydroxyethyl)-1'-methyl-spiro(2H-benzofuro[2,3-a]quinolizine)-2,4'(1'H-pyrimidin-2'(3'H)-one) as a white crystalline solid. m.p. 212°–213° C.

EXAMPLE 37

(2SR,10bSR)-1,3,4,5'6,6',7,10b-octahydro-1',3'-dimethyl-spiro(2H-thieno[2,3-a]quinolizine)-2,4'(1'H-pyrimidin-2'(3'H)-one)

Step A: Preparation of (E,Z)-2-carbomethoxymethylidine-1,3,4,6,7,10b-hexahydrothieno[2,3-a]quinolizine A mixture of 0.191 g (1 mmol) of (10bSR)-1,3,4,6,7,12b-hexahydrothieno[2,3-a]quinolizin-2-one, 0.728 g (4 mmol) of trimethylphosphonoacetate and 0.668 g (4 mmol) 24% potassium hydride were reacted employing the procedure substantially as described in Example 24, Step A to give 0.138 g (52.3%) of (E,Z)-2-carbomethoxymethylidine-1,3,4,6,7,10b-hexahydrothieno[2,3-a]quinolizine as a yellow oily solid.

Step B: Preparation of (2RS,10bSR)-N-methyl-2-(2-methylamino-1,3,4,6,7,10b-hexahydrothieno[2,3-a]quinolizin-2-yl)acetamide Employing the procedure substantially as described in Example 27, Step A, 0.46 g (1.7 mmol) of (E,Z)-2-carbomethoxymethylidin-1,3,4,6,7,10b-hexahydrothieno[2,3-a]quinolizine was reacted using 15 ml methylamine and 10 ml ethanol to give 0.125 g (25%) of (2RS,10bSR)-N-methyl-2-(2-methylamino-1,3,4,6,7,10b-hexahydrothieno[2,3-a]quinolizin-2-yl)acetamide as a brown oil after purification by medium pressure column chromatography.

Step C: Preparation of (2RS,10bSR)-2-methylamino-2-(2-methylaminoethyl)-1,3,4,6,7,10b-hexahydrothieno[2,3-a]quinolizine A mixture of 0.125 g (0.43 mmol) of (2RS,10bSR)-N-methyl-2-(2-methylamino-1,3,4,6,7,10b-hexahydrothieno[2,3-a]quinolizin-2-yl)acetamide and 0.51 ml (1.72 mmol) of 3.4M sodium bis(2-methoxyethoxy)aluminum hydride were reacted employing the procedure substantially described in Example 27 Step B to give 0.07 g (59%) of (2RS,10bSR)-2-methylamino-2-(2-methylaminoethyl)-1,3,4,6,7,10b-hexahydrothieno[2,3-a]quinolizine as a brown oil.

Step D: Preparation of (2SR,10bSR)-1,3,4,5'6,6',7,10b-octahydro-1',3'-dimethyl-spiro(2H-thieno[2,3-a]quinolizine)-2,4'(1'H)pyrimidin-2'-(3'H)-one Employing the procedure substantially described in Example 27, Step C, 0.07 g (0.25 mmol) of (2RS,10bSR)-2-methylamino-2-(2-methylaminoethyl)-1,3,4,6,7,10b-hexahydrothieno[2,3-a]quinolizine and 0.082 g (0.5 mmol) of 1,1'-carbonyldiimidazole were reacted to give 0.037 g (48.3%) of (2SR,10bSR)-1,3,4,5',6,6',7,10b-octahydro-1',3'-dimethyl-spiro(2H-thieno[2,3-a]quinolizine)-2,4'(1'H pyrimidin-2'-(3'H)-one) after purification by spinning disc chromatography, from which was made the hydrochloride monohydrate salt. m.p. 179°–181° C.

EXAMPLE 38

(2SR,12bSR)-1,3,4,5',6,6',7,12b-octahydro-2',6'-dimethyl-spiro(2H-benzofuro[2,3-a]quinolizine)-2,3'-(4'H-(2H-1,2,6)thiadiazine,1',1'-dioxide)

A mixture of 0.168 g (0.54 mmol) of (2RS,12bSR)-2-methylamino-2-(2-methylaminoethyl)-1,3,4,6,7,12b-hexahydrobenzo[b]furo[2,3-a]quinolizin and 0.109 g (1.08 mmol) of triethylamine in 10 ml methylene chloride was cooled to −78° C. under $N_2$. Sulfuryl chloride (0.144 g, 1.08 mmol) was reacted employing the procedure substantially as described in Example 12 to give 0.062 g (28%) of (2SR,12bSR)-1,3,4,5',6,6',7,12b-octahydro-2',6'-dimethyl-spiro(2H-benzofuro[2,3-a]quinolizine)-2,3'-(4'H-(2H-1,2,6)thiadiazine,1',1'-dioxide)hydrochloride m.p. 250° C. (dec).

EXAMPLE 39

(2SR,12bSR)-1,3,4,6,7,12b-hexahydro-spiro-(2H-benzothieno[2,3-a]quinolizin)-2,5'-(oxazolidin-2'-one)

Step A: Preparation of (2SR,12bSR)-2-aminomethyl-2-hydroxy-1,3,4,6,7,12b-hexahydrobenzo[b]thieno[2,3-a]quinolizine Into a 500 ml flask was placed 0.8 g (3.11 mmol) of 1,3,4,6,7,12b-hexahydrobenzo[b]thieno[2,3-a]quinolizin-2-one in 200 ml wet THF which had previously been saturated with methylamine at 0° C. To this mixture was added 1 g (6.21 mmol) of diethyl cyanophosphonate. The reaction was then carried out employing the procedure substantially as described in Example 16, Step A to give (2SR,12bSR)-2-aminomethyl-2-hydroxy-1,3,4,6,7,12b-hexahydrobenzo[b]thieno[2,3-a]quinolizine which was carried on without further purification.

Step B: Preparation of (2SR,12bSR) (1,3,4,6,7,12b-hexahydro-spiro-(benzo[b]thieno[2,3-a]quinolizin)-2,5'-(oxazolidin-2'-one)

A mixture of amino alcohol from Step A and 100 ml of toluene was treated with 0.645 g (3.98 mmol) 1,1'-carbonylidiimidazole employing the procedure substantially as described in Example 1, Step G to obtain 0.2 g (21%) (2SR,12bSR) (1,3,4,6,7,12b-hexahydro-spiro-(benzo[b]thieno[2,3-a]quinolizin)-2,5'-(oxazolidin-2'-one) from which was made the hydrochloride salt. m.p. 240° C. (dec).

EXAMPLE 40

(2SR,12bSR)-3'-Methyl-spiro(1,3,4,6,7,12b-hexahydrobenzo[b]thieno[2,3-a]quinolizin)-2,5'-(oxazolidin-2'-one)

Employing the procedure described in Example 3, (2SR,12SR)-spiro (1,3,4,6,7,12b-hexahydrobenzo[b]thieno[2,3-a]quinolizin)-2,5'(oxazolidin-2'-one) (Example 39) (35 mg, 0.1 mmole) gave 21 mg (57%) of the title compound as the hydrochloride, m.p. 280° C.

EXAMPLE 41

(2RS,12bSR)-1'-Methyl-spiro-(1,3,4,6,7,12b-hexahydro-2H-benzo[b]furo[2,3-a]quinolizine)-2,5'-(pyrrolidin-2'-one)

Step A: Preparation of (2RS,12bSR)-Ethyl-2-methylacetamido-1,3,4,6,7,12b-hexahydro-2H-benzo[b]furo[2,3-a]quinolizine-2-carboxylate (2RS,12bSR)-Ethyl-2-methylamino-1,3,4,6,7,12,b-hexahydro-2H-benzo[b]furo[2,3-a]quinolizine-2-carboxylate (Step B, Example 19) was dissolved in 5 ml of methylene chloride and 50 mg (0.49 mmol, 0.07 ml) of triethylamine was added followed by 39 mg (0.5 mmol, 0.035 ml) of acetyl chloride. After 6 hours at room temperature, this was diluted with saturated sodium bicarbonate and the product filtered and concentrated. The residue obtained was chromatographed (SiO$_2$,NH$_3$ saturated chloroform) to give 82 mg of the title compound as an oil. M+ =370.

Step B: Preparation of (2RS,12bSR)-1'-Methyl-spiro-(1,3,4,6,7,12b-hexahydro-2H-benzo[b]furo[2,3-a]quinolizine)-2,2'-(pyrrolidin-3',5'-dione)

(2RS,12bSR)-Ethyl-2-methylacetamido-1,3,4,6,7,12b-hexahydro-2H-benzo[b]furo[2,3-a]quinolizine-2-carboxylate 36 mg (0.102 mmol) was dissolved in 2 ml of DMSO and 23 mg (0.203 mmol) of potassium-t-butoxide was added. After 1.5 hour at room temperature the reaction was quenched with saturated NH$_4$Cl solution, made basic and washed with ethyl acetate. The organic phase was dried (Na$_2$SO$_4$), filtered and concentrated to give an oil which was chromatographed (SiO$_2$, 10% MeOH/CHCl$_3$) to give the title compound. M+(324).

Step C: Preparation of (2RS,12bSR,3'RS)-1'-Methyl-spiro-(1,3,4,6,7,12b-hexahydro-2H-benzo[b]furo[2,3-a]quinolizine)-2,2'-(3'-hydroxy pyrrolidin-5'-one)

(2RS,12bSR)-1'-Methyl-spiro-(1,3,4,6,7,12b-hexahydro-2H-benzo[b]furo[2,3-a]quinolizine)-2,2'-(pyrrolidin-3',5'-dione) 32 mg (0.1 mmol) was dissolved in 5 ml of ethanol and cooled to 0° C. To this was added 4 mg of NaBH$_4$. After 1 hour this was diluted with water and extracted with ethyl acetate which was dried (Na$_2$SO$_4$) filtered and concentrated to give 27 mg of the subject compound as a mixture of alcohols. M+(326).

Step D: Preparation of (2RS,12bSR,3'RS)-1'-Methyl-spiro-(1,3,4,6,7,12b-hexahydro-2H-benzo[b]furo[2,3-a]quinolizine)-2,2'-(3'-mesyloxy pyrrolidin-5'-one)

To 25 mg (0.076 mmol) of (2RS,12bSR,3'RS)-1'-Methyl-spiro-(1,3,4,6,7,12b-hexahydro-2H-benzo[b]furo-[2,3-a]quinolizine)-2,2'-(3'-hydroxy pyrrolidin-5'-one) dissolved in 5 ml of methylene chloride was added 10 mg (0.099 mmol, 0.014 ml) of triethylamine followed by 11 mg (0.099 mmol, 0.008 ml) of methanesulfonyl chloride. After 1 hour at 0° C. the solution was diluted with saturated NaHCO$_3$ solution and washed with methylene chloride which was dried (Na$_2$-

SO4) filtered and concentrated to give 27 mg (89%) of the title product which as a mixture of mesylates.

Step E: Preparation of (2RS,12bSR,)-1'-Methyl-spiro-(1,3,4,6,7,12b-hexahydro-2H-benzo[b]furo[2,3-a]quinolizine)-2,2'-(pyrrolid-3',4'-en-5'-one)

To a solution of (2RS,12bSR,3'RS)-1'-Methyl-spiro-(1,3,4,6,7,12b-hexahydro-2H-benzo[b]furo[2,3-a]quinolizine)-2,2'-(3'-meslyloxy pyrrolidin-5'-one) (32 mg, 0.076 mmol) in 2 ml of methylene chloride was added 12 mg (0.026 mmol) of 1,8-diazabicyclo[5.4.0]-undec-7-ene and the solution was warmed to 40° C. After 30 minutes the reaction was diluted with methylene chloride, washed with water, dried (Na2SO4), filtered and concentrated to a residue which was used directly in Step F. M+(308).

Step F: Preparation of (2RS,12bSR)-1'-Methyl-spiro-(1,3,4,6,7,12b-hexahydro-2H-benzo[b]furo[2,3-a]quinolizine)-2,5'-(pyrrolidin-2'-one)

To a solution of (2RS,12bSR)-1'-Methyl-spiro-(1,3,4,6,7,12b-hexahydro-2H-benzo[b]furo[2,3-a]quinolizine)-2,2'-(pyrrolid-3',4'-en-5'-one) (59 mg, 0.19 mmol) in 5 ml of ethanol was added 25 mg of 5% Palladium on charcoal and the reaction was charged with an atmosphere of hydrogen at 1 atmosphere. After 1.5 hour the reaction was filtered through celite, the filtrate was evaporated and the residue was chromatographed (SiO2, 10% MeOH/CHCl3) to yield 39 mg of the title compound. m.p. 189°-193° C. HCl salt trihydrate (MeOH) M+(310).

EXAMPLE 42

1,1',2'3,3'4,4',6,7,12b-Decahydro-4'-methanesulfonyl-spiro(2H-benzofuro(2,3-a)quinolizine-2,5'(5H-1,4-diazepin-7'(6'H)-one)monohydrochloride Step A: Preparation of 1,1',2',3,3',4,4',6,7,12b-decahydro-spiro-(2H-benzofuro(2,3-a)quinolizine)-2,5'-(5H-1,4-diazepin-7'(6'H)-one)

To a 10 ml round bottomed flask with stirring bar and argon inlet was added (E,Z)-2-carbomethoxymethylidine-1,3,4,6,7,12b-hexahydrobenzo[b]furo[2,3,-a]quinolizine (900 mg, 3.02 mmol), 4.5 ml of methanol and ethylenediamine (8.09 g, 134.6 mmol), freshly distilled from calcium hydride. This mixture was stirred at room temperature for 40 hours, then diluted with ethylacetate and washed with water and brine. Drying (Na2SO4), filtration, removal of the solvent in vacuo followed by chromatographed of the residue on 25 g of silica gel using 6% methanol in chloroform as eluant provided 550 mg of intermediate diazepinone.

Step B: Preparation of 1,1',2'3,3'4,4',6,7,12b-decahydro-4'-methanesulfonyl-spiro-(2H-benzofuro(2,3-a)quinolizine)-2,5'-(5H-1,4-diazepin-7'(6'H)-one) monohydrochloride To a 25 ml round bottomed flask containing intermediate diazepinone from Step A (396 mg, 1.21 mmol was added 30 ml of dry methylene chloride and diisopropylethylamine (2.12 ml, 12.17 mmol). The resulting solution was cooled to 0° C. in an ice bath and methanesulfonyl chloride (0.47 ml, 6.07 mmol) was added in one portion. The mixture was stirred at 0° C. for 30 minutes then diluted with methylene chloride and washed with water and brine. Drying (Na2SO4), filtration, removal of the solvent in vacuo, followed by chromatography of the residue on 100 g of silica gel using 5% methanol in chloroform as eluant provided 134 mg of the title compound free base. The hydrochloride salt was crystallized from ethanolic HCl and dried in vacuo. m.p. 282°-285° C.

EXAMPLE 43

Pharmaceutical Formulation

| Ingredient | Mg/Capsule |
|---|---|
| (2RS,12bSR)-3'-methyl-spiro (1,3,4,6,7,12b-hexahydro-benzo[b]furo[2,3-a]quinolizine)-2,4'-imidazolidin-2'-one | 6 |
| starch | 87 |
| magnesium stearate | 7 |

The active ingredient, starch and magnesium stearate are blended together. The mixture is used to fill hard shell capsules of a suitable size at a fill weight of 100 mg per capsule.

EXAMPLE 44

| Ingredient | Mg/Capsule |
|---|---|
| (2SR,12bSR)-1',3'-dimethyl-spiro (1,3,4,6,7,12b-hexahydro-benzo[b]-furo[2,3-a]quinolizine)-2,4'-(5',6'-dihydro-1',3'-diazin-2'-one) | 6 |
| starch | 87 |
| magnesium stearate | 7 |

What is claimed is:

1. A method of treating at least one condition diabetes, hypertension, ocular hypertension, abnormal platelet aggregation, obesity, and abnormal gastrointestinal motility, when said condition is responsive to an $\alpha_2$ adrenoceptor antagonist, which comprises administering to a patient, in need of such treatment, an $\alpha_2$ adrenoceptor antagonist amount of a compound, or a pharmaceutically acceptable salt thereof, of the structural formula:

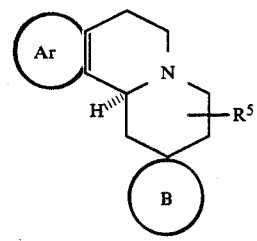

wherein

Ar represents an aromatic heterocycle selected from $R^2,R^2$-benzo[b]furo-,$R^1,R^2$-benzo[b]thieno-, thieno-, furo-; $R^1,R^2$-benzo, $R^1,R^2$-pyridino, thiazolo, imidazo, and pyrazolo; $R^1$ and $R^2$ are independently:

(1) hydrogen,
(2) halo,
(3) hydroxy,
(4) $C_{1-3}$alkoxy, or
(5) $C_{1-6}$alkyl;

B represents a spiroheterocycle of 4-7 members selected from

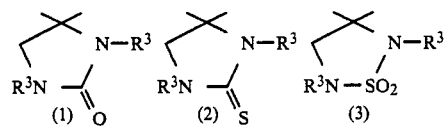
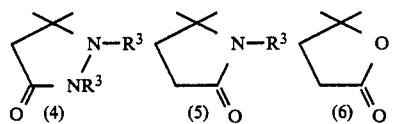
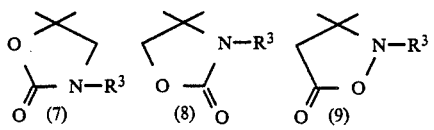
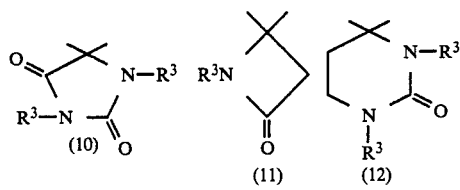
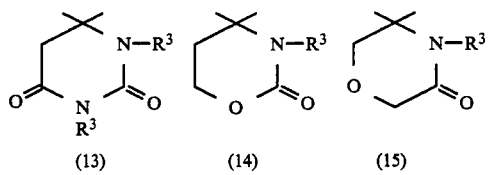
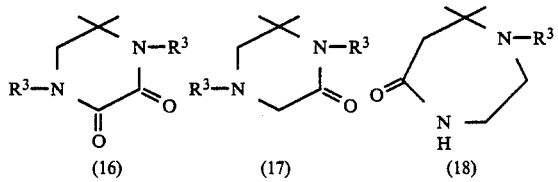

R³ is
(1) hydrogen,
(2)

wherein R is hydrogen or C₁₋₃alkyl,
(3) Cl₁₋₆alkyl, either unsubstituted or substituted with one or more of;
(a) hydroxy,
(b) carboxy,
(c) C₁₋₃alkoxycarbonyl,
(d) halo,
(e) C₁₋₃alkoxy,
(f) —CONR⁶R⁷, wherein R⁶ and R⁷ are the same or different and are hydrogen or C₁₋₅alkyl, or joined together directly to form a 5–7 membered ring selected from pyrrolidino, and piperidino or through a heteroatom selected from O, N and S, to form a 6-membered heterocycle selected from morpholino, piperazino, and N—C₁₋₃alkylpiperazino with the nitrogen to which they are attached,
(g) —NR⁶R⁷,

(i) —SO₂NR⁶R⁷ or
(j) —SO₂(C₁₋₃alkyl); and
R⁵ is
(1) hydrogen,
(2) C₁₋₆alkyl, either unsubstituted or substituted with one or more of
(a) —OR⁸, wherein R⁸ is
(i) H, or
(ii) C₁₋₆alkyl
(b) —NR⁸COR⁸, or
(c) —CO₂R₈,
(3) —CO₂R⁸, or
(4) CONR⁶R⁷.

2. A method of treating at least one condition of diabetes, hypertension, ocular hypertension, abnormal platelet aggregation, obesity, and abnormal gastrointestinal motility, when said condition is responsive to an α₂ adrenoceptor antagonist, which comprises administering to a patient, in need of such treatment, an α₂ adrenoceptor antagonist amount of a compound, or a pharmaceutically acceptable salt thereof, of (2R,12bS)-1′,3′-dimethylspiro(1,3,4,6,7,12b-hexahydrobenzo[b-]furo[2,3-a]quinolizin)-2,4′-imidazolidin-2′-one; or (2S,12bS)-1′,3′-dimethylspiro-(1,3,4,6,7,12b-hexahydrobenzo-[b]-furo[2,3-a]quinolizin)-2,4′-(5′,6′-dihydro-1′H-pyrimidin-2′(3′H)-one.

3. The method of claim 1, wherein Ar is R¹,R²-benzo[b]furo, R¹R²-benzo[b]thieno, thieno, benzo or furo.

4. The method of claim 1, wherein Ar is R¹,R²-benzo[b]furo, R¹,R²-benzo[b]thieno- or benzo-; R¹ and R² are hydrogen or halo; B is a spiroimidazolidin-2-one or spiro-(5,6-dihydro-1H-pyrimidin-2(3H)-one); R³ is C₁₋₆alkyl; and R⁵ is hydrogen or C₁₋₆ alkyl.

5. The method of claim 1, wherein R¹ and R² are hydrogen, R³ is methyl, and R⁵ is hydrogen.

6. The method of claim 1, wherein Ar is benzo[b-]furo-, R³ is —CH₃.

* * * * *